US012588831B2

(12) United States Patent     (10) Patent No.:    US 12,588,831 B2

DeArmond et al.        (45) Date of Patent:      Mar. 31, 2026

(54) METHOD FOR MONITORING LUNG INTEGRITY

(71) Applicant: THE BOARD OF REGENTS OF THE UNIVERSITY OF TEXAS SYSTEM, Austin, TX (US)

(72) Inventors: Daniel T. DeArmond, Shavano Park, TX (US); Lucas M. Holt, Austin, TX (US); Andrew P. Wang, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1239 days.

(21) Appl. No.: 17/051,770

(22) PCT Filed: Apr. 30, 2019

(86) PCT No.: PCT/US2019/029861

§ 371 (c)(1),
(2) Date: May 9, 2022

(87) PCT Pub. No.: WO2019/213051

PCT Pub. Date: Nov. 7, 2019

(65) Prior Publication Data

US 2021/0236018 A1     Aug. 5, 2021

Related U.S. Application Data

(60) Provisional application No. 62/665,185, filed on May 1, 2018.

(51) Int. Cl.
    *A61B 5/085*       (2006.01)
    *A61B 5/00*        (2006.01)
    (Continued)

(52) U.S. Cl.
    CPC .............. *A61B 5/085* (2013.01); *A61B 5/037* (2013.01); *A61B 5/1107* (2013.01);
    (Continued)

(58) Field of Classification Search
    CPC ............ A61M 1/73; A61M 1/84; A61M 1/69; A61M 1/732; A61M 1/74; A61M 1/75; A61M 2025/105; A61M 2025/1075; A61M 2025/1079; A61M 2202/0492; A61M 2205/3324; A61M 2209/082; A61M 2210/101; A61M 2210/105;
    (Continued)

(56) References Cited

U.S. PATENT DOCUMENTS 10,842,560 B2 *   11/2020   Panescu ............. A61B 18/1492
2002/0193700 A1   12/2002   Bohm et al.
(Continued)

OTHER PUBLICATIONS

International Search Report and Written Opinion issued in corresponding International application No. PCT/US2019/029861 dated Sep. 10, 2019.

*Primary Examiner* — Jon Eric C Morales

(57) ABSTRACT

The present invention relates to systems and methods for monitoring impedance from a sensor in the chest of a subject to determine the status of lung inflation or presence of pneumothorax in the subject, the presence of pulmonary edema, the status of regional lung ventilation, and the status of cardiac contractility.

12 Claims, 16 Drawing Sheets

(51) Int. Cl.
      *A61B 5/03*        (2006.01)
      *A61B 5/11*        (2006.01)
      *A61M 1/04*        (2006.01)
(52) U.S. Cl.
      CPC .......... *A61B 5/4839* (2013.01); *A61B 5/4878*
              (2013.01); *A61B 5/6847* (2013.01); *A61M*
                                              *1/04* (2013.01)
(58) Field of Classification Search
      CPC ...... A61M 2210/1053; A61M 25/0045; A61M
              25/10; A61M 25/1002; A61M 27/00;
              A61B 18/1492; A61B 2018/00577; A61B
              2018/1472; A61B 2218/007; A61B
              5/0536; A61B 5/0538; A61B 5/08; A61B
              17/12136; A61B 18/042; A61B 2017/003;
              A61B 2017/22038; A61B 2018/00119;
              A61B 2018/0016; A61B 2018/0022;
              A61B 2018/00285; A61B 2018/00291;
              A61B 2018/00351; A61B 2018/00422;
              A61B 2018/00541; A61B 2018/00583;
              A61B 2018/00642; A61B 2018/00648;
              A61B 2018/00702; A61B 2018/00744;
              A61B 2018/00791; A61B 2018/00863;
              A61B 2018/00875; A61B 2018/00982;
              A61B 2018/048; A61B 2018/1213; A61B
              2018/124; A61B 2018/1253; A61B
              2018/1273; A61B 2018/1425; A61B
              2018/143; A61B 2018/1432; A61B
              2018/1467; A61B 2018/162; A61B
              2034/2051; A61B 2034/2053; A61B
              2034/2061; A61B 2034/2063; A61B
              2090/306; A61B 2090/376; A61B
              2090/378; A61B 2090/3782; A61B
              2090/3966; A61B 2218/002; A61B
              2562/0204; A61B 2562/043; A61B 34/20;
              A61B 5/00; A61B 5/01; A61B 5/05;
              A61B 5/065; A61B 5/068; A61B 5/0816;
              A61B 5/085; A61B 5/086; A61B 5/1073;
              A61B 5/14503; A61B 5/14539; A61B
              5/1473; A61B 5/287; A61B 5/318; A61B
              5/33; A61B 5/4205; A61B 5/4211; A61B
              5/4233; A61B 5/4238; A61B 5/4836;
              A61B 5/6852; A61B 5/6898; A61B
              5/7282; A61B 5/746; A61B 7/00; A61B
              7/003; A61B 7/008; A61B 7/04; A61B
              90/39; A61J 15/0084; A61J 15/0088
      See application file for complete search history.

(56)                    References Cited

U.S. PATENT DOCUMENTS

2014/0018696 A1      1/2014  DeArmond
2015/0320916 A1*    11/2015  Croteau .................. A61M 1/73
                                                            604/327

* cited by examiner

Pulse width modulation (%) versus detected resistance (ohms) for air leak of 0 liters/min Pulse width modulation (%) versus detected resistance (ohms) for air leak of 1 liters/min pulse width modulation (%)

detected resistance (ohms)

time (sec)

Pulse width modulation (%) versus detected resistance (ohms) for air leak of 4 liters/min

METHOD FOR MONITORING LUNG INTEGRITY

PRIORITY PARAGRAPH

This Application is a national phase application under 35 U.S.C. § 371 of International Application No. PCT/US2019/029861, filed Apr. 30, 2019, which claims priority to U.S. Provisional Application Ser. No. 62/665,185 filed May 1, 2018, which is incorporated herein by reference in its entirety.

BACKGROUND

Anatomic and physiologic changes to the lung, pleural space (the space around the lungs), the heart, and/or pericardial space (the space around the heart) due to surgery, blunt or penetrating trauma involving the chest, or other non-surgical and non-traumatic conditions affecting the lungs or heart may result in substantial impairment of the function of the lungs and/or heart leading to patient morbidity and mortality. Chest tubes, i.e., drainage catheters that are placed in the pleural and/or pericardial space in contact with the heart or lung, are commonly used in these clinical scenarios. Changes affecting the internal organs and anatomy of the chest may occur rapidly leading to rapid pathologic changes. Real-time monitors of the internal organs of the chest are in current clinical use to help minimize morbidity and mortality. However, real-time, continuous monitoring of the lung and pleural and pericardial spaces in general is carried out only indirectly by monitoring of non-specific vital signs, or when direct monitoring of the lung, pleural space and/or pericardial space is performed it is not continuous or in real-time, for example when radiologic examination of the lungs is performed or when echocardiogram to assess the pericardial space is performed.

There is a clear clinical need for a real-time, continuous monitoring of lung/pleural/hear/pericardial pathology in which direct measurements from the lung/pleural space/pericardial space are performed.

SUMMARY

Embodiments described herein relate to systems and methods for measuring and monitoring the impedance of a sensor in the chest of a subject and adjusting the environment to maintain appropriate conditions for patient well-being, e.g., inflation of the lungs. In certain aspects the systems and methods described herein can be used to detect the presence of a pneumothorax or a collapsed lung by the measurement of impedance signals generated by a sensor in the chest. The signals can be generated by monitoring electrical resistance and impedance directly in the pleural space and/or from the surface of the lung via electrode(s) and/or sensor(s) located in the pleural space. As used herein "electrode" refers to a conductor used to establish electrical contact with a nonmetallic part of a circuit, e.g., an organ or the lung surface. In certain aspects electrodes are small metal discs, wires, or looped wire usually made of stainless steel, tin, gold, titanium, silver or an alloy of one or more metal, or some other non-metallic electrically conducting substance and may or may not be covered with a silver chloride coating.

A sensor for monitoring lung integrity can include, but is not limited to a sensor head having a proximal end operatively coupled to a transmission lead and a distal end coupled to a protective cap, the sensor head comprising at least four bare or non-embedded sensor wires forming arcs from the transmission lead to the protective cap, the sensor wires each being coupled to the protective cap and forming a convex shape that is configured to contact the curvature of the lung surface and a concave shape that is configured to face the inner chest wall of a subject. In certain aspects the sensor head is attached to a support surface. The support surface can be a non-conducting polymer. In certain aspects the support surface is configured to present the sensor wires to the surface of the lung. In certain aspects the support surface is configured to present the sensor wires to the inner surface of the rib cage facing away from the lung surface. The support can have a convex or concave shape. The sensor wire, that is the non-embedded portion of the wire, can be about 0.1, 0.2, 0.5, to 0.6, 1.0, 1.5, 2, 3, 4, 5, 10 mm in length. The sensor wire can have a diameter of about 0.01, 0.2, 0.3 to 0.3, 0.4, 0.5, 1, 2, 3, 4, 5, 10 mm. In certain aspects the sensor wire is made of a conductive metal or metal alloy. In certain aspects the sensor wire is copper or a copper alloy. In certain aspects the sensor wire is steel, titanium, gold, silver or some other biologically inert metal or alloy or some other non-metallic electrically conducting material. The sensor wire can be curved and have a radius of curvature of about 0.5 to 10 mm. In certain aspects sensor wires diverge from each other once leaving the transmission lead until the apex of the arc where the wires then converge and are coupled to the protective cap. In a further aspect sensor wires have a minimal spacing of at least 0.1 mm and a maximum spacing up to 10 cm. In certain embodiments the sensor wires are parallel to each other once they leave the transmission lead and are coupled to the protective cap. The transmission lead is configured to couple the sensor head to a detector. In certain aspects the detector comprises a voltmeter or a bioimpedance device.

Certain embodiments are directed to a method for monitoring lung integrity in a subject comprising inserting an intrapleural sensor into the pleural space of a subject wherein the sensor head contacts the exterior surface of the lung or the interior surface of the rib cage or one sensor contacting the lung with a second contacting the inner surface of the rib cage, the sensor(s) being operatively coupled to a microcontroller that is programmed to monitor signals from the sensor, the microcontroller being operatively coupled to an intervention device circuit such as a suction control circuit.

In certain aspects a sensor can include a pressure sensor including but not limited to: piezoresistive strain gauges, capacitive pressure sensors, electromagnetic pressure sensors, piezoelectric pressure sensors, strain-gauge pressure sensors, optical pressure sensors which may or may not be based on laser interferometry, potentiometric pressure sensors, resonant pressure sensors, thermal pressure sensors, or ionization pressure sensors. In certain aspects the sensor is based on electrocardiogram signals obtained from the surface of internal tissues.

Certain embodiments are directed to a lung integrity monitoring system comprising one or more electrodes or sensors operatively coupled to a microcontroller that is programed to monitor the sensors and to control intervention mechanisms, such as a suction device, via intervention control circuit. In certain aspects the sensor is connected to a voltmeter that can be used to determine the impedance between two or more electrodes positioned on the surface of the lung. In certain aspects the electrodes are connected to the same transmission lead that is positioned across the chest wall and connects the electrode(s) or sensor(s) to the microcontroller for monitoring and/or detection. In other aspects each electrode or sensor is connected to the detector by individual transmission leads. The microcontroller is configured to monitor changes in impedance as well as compare real-time impedance patterns with reference impedance patterns or predetermined thresholds. A reference impedance pattern(s) can be a baseline reading from the subject being monitored or a reference pattern from another normal and/or abnormal subject(s). A baseline impedance pattern indicates a normal lung condition where as an impedance pattern that is altered or abnormal indicates the presence or formation of an abnormal condition. In certain aspects the abnormal impedance signal is an impedance flat-line or rail that comprises a series of impedance measurements that increase at least 5 fold (e.g., >1000 ohms) over a base line impedance (e.g., 200 ohms). In certain aspects the impedance measurements registers an infinite impedance. Cessation of current flow between the electrodes is manifested in the impedance measuring device registering a flat line or rail at the maximum possible impedance for that device (e.g., 1600 ohms, though some devices may register infinite impedance in negative values, e.g., −1600 ohms). In certain aspects the detection of such an abnormal impedance pattern, including a large increase in impedance or a flat-line or rail at the maximum impedance value for the impedance measuring device, will be detected by the microcontroller and signals for corrective measures sent to a suction control circuit. In certain aspects the microcontroller can also be programmed to trigger or send an alarm or alert. In certain aspects the alarm or alert is sent to medical personnel via an electronic communication such as a text message or the like. In certain aspects the alarm or alert can be or includes an audible alarm or alter that can be heard by medical personnel that are locally situated (e.g., in the same room or proximity) or remote (e.g., at a monitoring station or the like).

Advantages of the system and methods include, but are not limited to: Continuous real-time monitoring of lung and pleural pathology, in contrast to intermittent monitoring possible by chest x-rays or ultrasound which may be delayed when needed. Use of raw impedance data is an additional advantage of the system and methods, other impedance devices on the market require complex mathematical assumptions to arrive at meaningful data but in patents with numerous medical conditions these assumptions may not apply and the signal to noise ratio becomes significantly degraded because the current system and methods derive lung impedance values directly from the lung, no such assumptions are required. This system may or may not incorporate artificial intelligence to tailor chest tube suction therapy in the absence of direct clinician involvement. This allows for rapid interventions to be implemented in emergency situations when the obtaining of medical history and physical exam by clinicians or other diagnostic modalities may not be immediately available, and tailoring of suction in non-emergency situations to optimal levels in a way not currently readily feasible due to clinician time constraints. Suction therapy on chest tubes can cause trauma to the lung so minimizing suction is an advantage, but clinicians rarely have the time to perform this optimization as it would require extended periods of time up to hours at a patient's bedside making small adjustments to a suction device. Or the system and methods described here could allow for suction to be altered with different phases of the respiratory cycle such as activating suction during inspiration and deactivating suction during the expiratory cycle or in other ways modulating suction based on the respiratory cycle.

The system and methods also can allow for the measurement of regional lung ventilation and may be used in a physiologic feedback loop to tailor mechanical ventilator therapy by altering delivered tidal volume and/or pressure or altering modes of mechanical ventilation by a mechanical ventilator to maximize ventilation and minimize lung injury, with or without using artificial intelligence. In certain embodiments the system would detect the peak electrical resistance, $R_P$ or the peak electrical impedance, $Z_P$ and the trough resistance, $R_T$ or the trough impedance, Zr of the sinusoidal respiratory electrical resistance waveform from the pleural impedance sensor and calculate the amplitude by $R_P$–$R_T$ or $Z_P$–$Z_T$, respectively. The system would additionally communicate with the mechanical ventilator to obtain the value for peak inspiratory pressure, $P_{IP}$, which is measured by the ventilator. The system would then calculate an aeration index, AI, by the following equation: $AI=(R_P–R_T)/P_{IP}$ or by $AI=(Z_P–Z_T)/P_{IP}$. The system would alter tidal volume and/or pressure delivered by the mechanical ventilator and calculate values for AI until the value for AI was maximized and then keep the tidal volume and/or pressure at that level to maximize ventilation and minimize barotrauma. Neural networks could be used to facilitate rapid identification of the maximal value for AI.

The system and methods also can allow for the measurement of lung edema and may be used in a physiologic feedback loop functionality to tailor diuretic therapy or inotropes again with or without using artificial intelligence.

The system and method can also allow for the measurement of heart contractility by placing the sensor in contact with the heart or the pericardium instead of the lung and may be used in a physiologic feedback loop to tailor vasopressor, inotrope, diuretic, or intravenous fluid therapy again with or without using artificial intelligence.

Certain embodiments are directed to methods for detecting regional lung ventilation in a subject. The subject can be (i) ventilated by a mechanical ventilator, (ii) have a chest tube or other device with a built-in impedance measuring circuit implanted into the pleural space and/or (iii) have a pressure sensor measuring intra-airway pressure. The method can include monitoring the subject with a monitoring system comprising a sensor for measuring airway pressure, a pleural-based impedance measuring circuit, a mechanical ventilator control circuit, and microcontroller. Monitoring steps can comprise one or more of the following: (a) determining initial intra-airway pressure, initial peak lung impedance, initial lung average impedance, and initial amplitude of the respiratory impedance waveform measured by the sensors in the chest cavity to determine the degree of regional lung ventilation and calculating a value for the aeration index (AI) as given by: $(R_P–R_T)/P_{IP}$ or by $(Z_P–Zr)/P_{IP}$; (b) reducing or increasing ventilator tidal volume according to a pre-determined algorithm after a pre-determined period of time; (c) determining intra-airway pressure, peak lung impedance, average lung impedance, and amplitude of the respiratory impedance waveform and calculating the value for aeration index (AI) after tidal volume is reduced or increased and determine whether regional lung ventilation is improved or diminished with respect to intra-airway pressure; and (d) continue monitoring if regional lung ventilation is improved with respect to intra-airway pressure based on the value for AI or reducing or increasing tidal volume according to a pre-determined algorithm for a pre-determined period of time and repeat steps (b) and (c).

Other embodiments are directed to methods for detecting pulmonary edema in a subject having a chest tube or other device implanted into the pleural space using a monitoring system that includes one or more components selected from an impedance measuring circuit, a control circuit controlling diuretic medication and/or inotrope and/or intravenous fluid administration, and microcontroller to perform one or more steps including: (a) determining initial impedance as measured by a sensor in the chest cavity to determine the degree of pulmonary edema; (b) administering diuretic medication and/or inotropes and/or intravenous fluids by a pre-determined algorithm after a pre-determined period of time; (c) determining impedance after diuretic medication and/or inotrope and/or intravenous fluid delivery and determine whether pulmonary edema is decreased; and (d) continue monitoring if pulmonary edema is decreased or administer diuretic medications and/or inotropes and/or intravenous fluids according to a pre-determined algorithm for a pre-determined period of time and repeat steps (b) and (c).

Certain embodiments are directed to methods for detecting cardiac contractility in a subject having a chest tube or other device implanted into the pleural or pericardial space using a monitoring system comprising an impedance measuring circuit, a control circuit controlling diuretic medication and/or inotrope and/or vasopressor and/or intravenous fluid administration, and microcontroller by performing the steps comprising: (a) determining initial impedance as measured by a sensor in the chest cavity to determine the degree of cardiac contractility; (b) administering diuretic medication and/or inotropes and/or vasopressors and/or intravenous fluids by a pre-determined algorithm after a pre-determined period of time; (c) determining impedance after diuretic medication and/or inotrope and/or vasopressor and/or intravenous fluids delivery and determine whether cardiac contractility is increased; and (d) continue monitoring if cardiac contractility is increased or administer diuretic medications and/or inotropes and/or vasopressors and/or intravenous fluids according to a pre-determined algorithm for a pre-determined period of time and repeat steps (b) and (c).

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1:
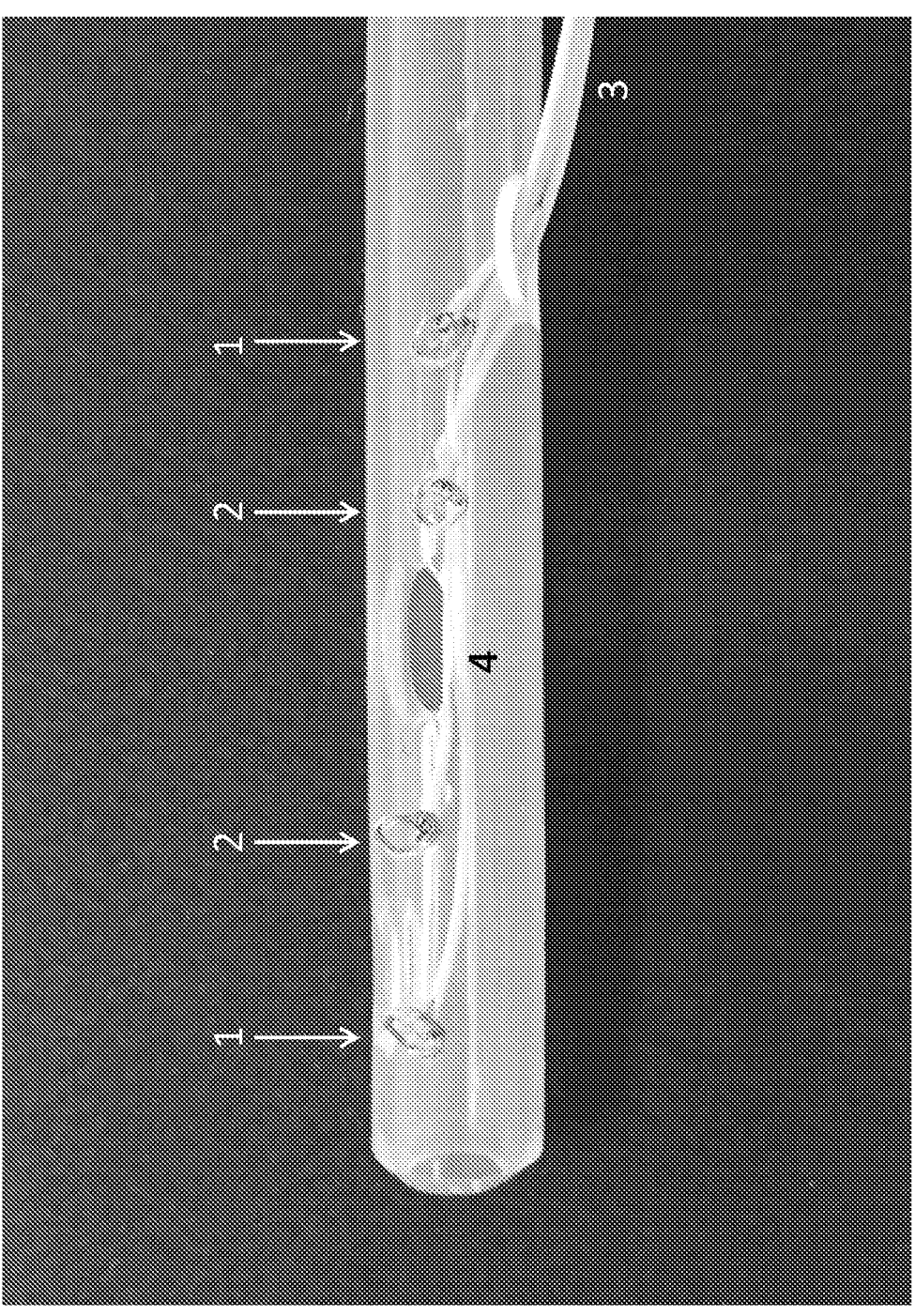
FIG. 1 illustrates a close-up view of the electrical contact sensors embedded in the distal end of a cylindrical chest tube.

Organs, tissue, and fluid in a human body possess an ability to conduct electricity due to their components and environment. A body is composed of cells, fluid, and/or air compartments that include a mixture of electrically conductive and resistive components. The mixture of conductive and resistive components determines the electrical properties of a given environment or portion of a body. Impedance, as used herein, refers to the ability to resist electrical currents and consists of two components: resistance and capacitive reactance. Cells, fluid, and/or air spaces all contribute to the electrical impedance that a given location, environment, organ, or tissue exhibits. When physiological changes occur at a particular location in the body the electrical impedance at that location may be measurably altered.

Pleural, pulmonary or cardiac pathology has the potential to be rapidly detrimental to the health of patients if not fatal by affecting the function of the lungs, pleural space, heart and/or pericardium. No real-time continuous monitoring system that takes readings directly from the surface of the lung or pleural space or pericardium is currently available. Chest tubes are commonly in use in pleural, pulmonary, or cardiac pathology and come into direct contact with the lung, pleural space, or heart/pericardium, but these tubes are not being used as sensors or to gather data; alternatively, sensors placed within the pleural space or pericardium could function independently of chest tubes. Electrical impedance/resistance measurement can be used to identify pathologic changes to the lung/pleural space (e.g., pneumothorax) due to the inherent electrical resistance of the air-filled lung. Electrical impedance/resistance measurement can be used to identify pathologic changes to the heart/pericardial space due to the inherent electrical resistance patterns of the beating heart.

A pneumothorax is an abnormal collection of air or gas in the pleural space that causes an uncoupling of the lung from the chest wall. Like pleural effusion (liquid buildup in the pleural space), pneumothorax may interfere with normal breathing. A primary pneumothorax is one that occurs spontaneously without an apparent cause and in the absence of significant lung disease, while a secondary pneumothorax occurs in the presence of existing lung pathology. A pneumothorax can be caused by physical trauma to the chest, or as a complication of medical or surgical intervention. In some cases the amount of air in the chest increases markedly when a one-way valve is formed by an area of damaged tissue, leading to a tension pneumothorax. This condition is a medical emergency that can cause steadily worsening oxygen shortage and low blood pressure. Unless detected and reversed by effective treatment, these sequelae can progress and cause death. Symptoms typically include chest pain and shortness of breath. Diagnosis of a pneumothorax by physical examination alone can be difficult or inconclusive, so a chest radiograph or computed tomography (CT) scan is usually used to confirm its presence.

Because the lungs are an inherently electrically resistive organ owing to the presence of air within the pulmonary alveoli (lung air sacs), the measurement of electrical resistance/impedance from the lung has been suggested as a sensitive detector of lung pathology and devices which measure electrical resistance/impedance from the lung are presently commercially available. Sensors can be inserted in the pleural space (i.e., pleural sensors) and be coupled to a detector by a transmission lead. The transmission lead can connect one or more sensors to a measurement determining unit or detector. Sensors may transmit data to a microcontroller. The microcontroller can be configured to produce a therapeutic intervention when the impedance/resistance deviates beyond a pre-selected range or to monitor the impedance/resistance over time, thus detecting and correcting alterations in the environment surrounding a sensor. Thus, the microcontroller forms part of an impedance monitoring circuit.

In one embodiment, the sensor can include, but is not limited to one or more bare metal wires configured in such a way as to promote contact of the wires with the surface of the lung or with the surface of the chest wall, diaphragm, heart or pericardium.

In one embodiment, the sensor or sensors are embedded in a thoracostomy tube; such tubes are generally made of soft plastic or silicone material and typically have one or more perforations in the distal end of the tube to facilitate the evacuation of fluid and/or air from the pleural or pericardial space.

To demonstrate the utility of electrical impedance measurements obtained directly from the surface of the lung to monitor lung integrity, an electrical impedance sensor was constructed that could be embedded in a chest tube to be placed into the pleural space of an experimental animal. An example of such a sensor is pictured in FIG. 1-3. The sensor consisted of electrical contact points fashioned from temporary cardiac pacing wires (A&E Medical, Farmingdale, NJ; cat. #021-001) (FIG. 1 (1,2)) which were connected to connecting wires (FIG. 1 (3)) with the contact end of the pacing wires (FIG. 1 (1,2)) embedded in the exterior surface of the distal end of a silicone chest tube (Medline, Northfield, Ill; cat. #AXX100028) (FIG. 1 (4)). The outer electrodes (FIG. 1 (1)) were configured to deliver electrical current (I) between them while the inner electrodes (FIG. 1 (2)) were configured to measure the voltage drop (V) between them.

Figure 2:
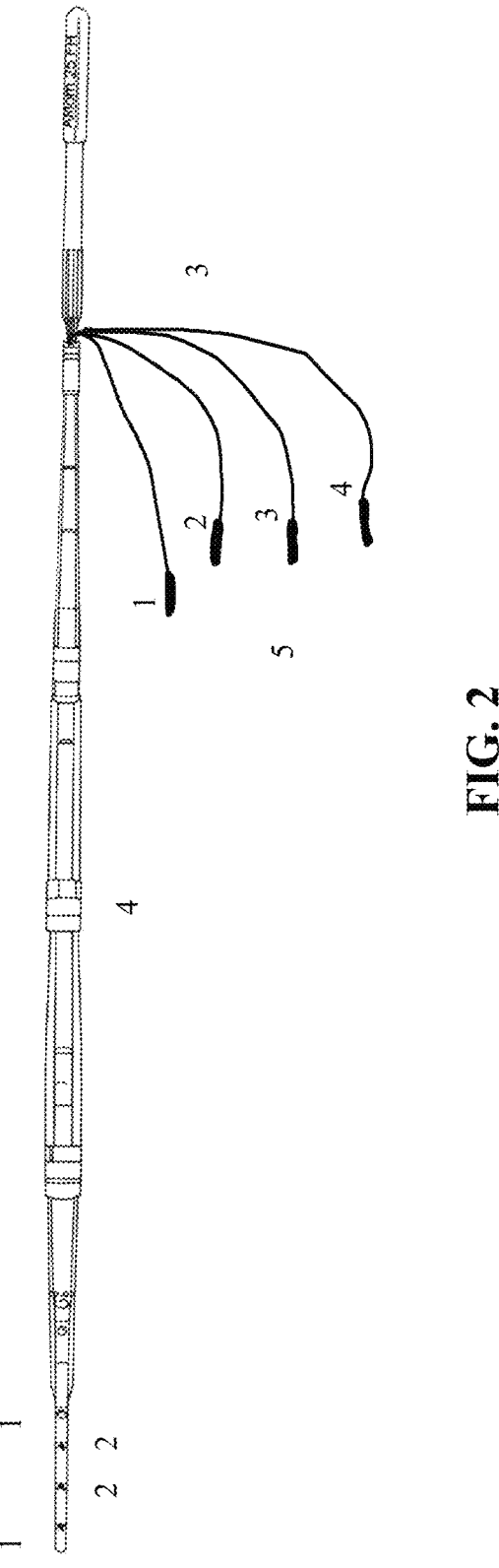
FIG. 2 illustrates electrical sensors embedded in a chest tube with wires being brought out along the length of the chest tube and connection points to the impedance measuring device.
Figure 3:
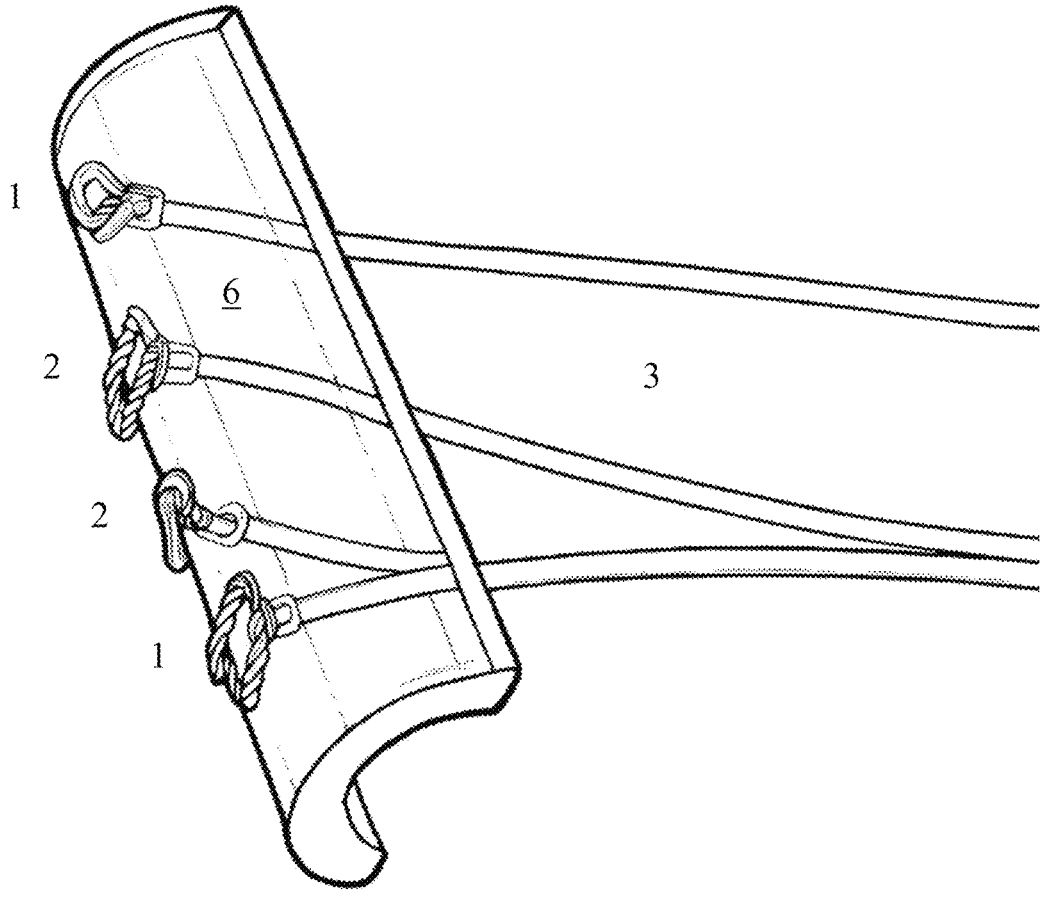
FIG. 3 illustrates the electrical contact sensors embedded in a non-conducting convex cap.

The connecting wires of the electrodes (FIG. 2 (3)) were brought along the outside of the length of the chest tube (FIG. 2 (4)) and connected to the impedance monitoring device (not shown) by the proximal pacing wire contact points (FIG. 2 (5)). The impedance measuring device (not shown) calculated impedance (Z) based on the formula: $Z=V/I$. Because the chest tube (FIG. 1 (4), FIG. 2 (4)) was made of silicone, an electrically non-conducting material, it functioned as an insulator to prevent the transmission of current between the electrodes in the absence of contact of the electrodes with tissue. Only in the case of all electrodes (FIG. 1 (1.2), FIG. 2 (1.2)) coming into contact with the same experimental animal tissue would current flow between them; without electrode tissue contact the current flow (I) would be zero rendering the measured value for impedance (Z) infinite. An alternative version of the sensor is shown in FIG. 3 and consisted of the bare pacing wire internal contact points (FIG. 3 (1.2)) embedded in an electrically insulating silicone cap (FIG. 3 (6)) and placed in the pleural space in contact with the lung surface and insulated against the chest wall of the experimental animal (not shown); the connecting wires of the electrodes (FIG. 3 (3)) were brought out of the experimental animal and connected to the impedance measuring device (not shown).

Figure 4:
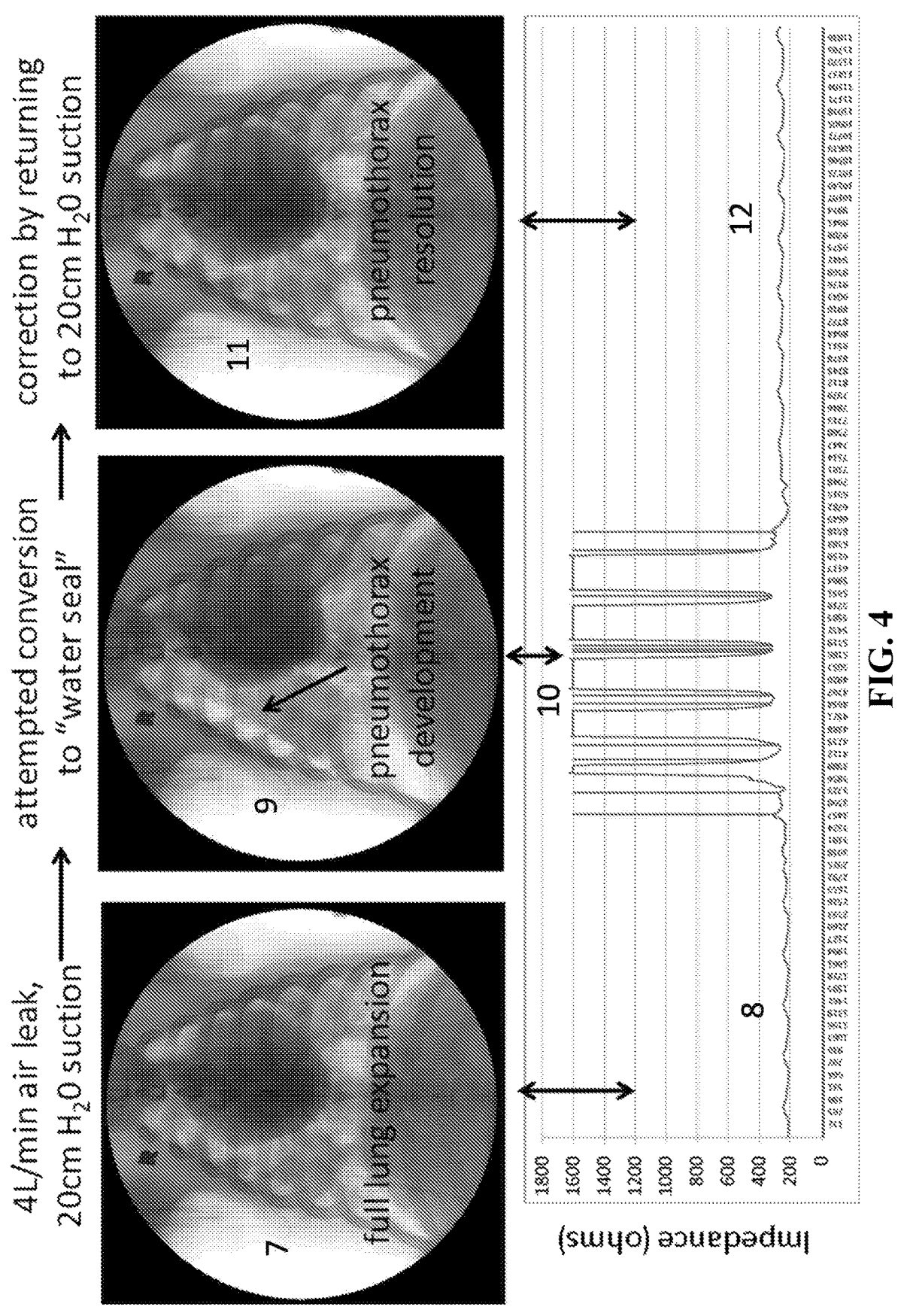
FIG. 4 illustrates experimental data of real time detection of lung collapse by impedance monitoring employing the electrode array shown in FIG. 1-3 placed into the pleural space in contact with the lung in a porcine model.

In order to provide a system that can continuously monitor a subject with a chest tube using impedance measurement (FIG. 1,2) or a free-standing intra-pleural impedance sensor (FIG. 3), the inventors previously have used a pig model of lung collapse to study and design an intervention system based on impedance measurements from a sensor positioned in the chest of an individual (illustrated in FIG. 4). This model consisted of two chest tubes located in the pleural space of the pig. One chest tube was meant to represent a conventional, therapeutic chest tube as used in human patients, i.e., which is connected to a suction device or alternatively only to a non-suction one way valve allowing any air present in the pleural space to be removed, maintaining full lung expansion. The second tube was used to introduce air into the pleural space at defined air-flows to mimic a pathologic air leak from the lung. The rationale for this model was that in human patients it is sometimes preferable from a clinical standpoint to provide suction via chest tubes in the pleural space to maintain full lung expansion while in other cases it is preferable not to use suction and place chest tubes simply to a one way valve allowing the natural motion of the lung to act as a pump to evacuate air out of the pleural space; this is due to the fact that suction therapy may be traumatic to the lung or impair lung healing in certain cases. However, it is not always clinically apparent which patients would benefit from which therapy and non-suction therapy carries a greater risk of allowing pneumothorax to develop. The inventors demonstrate that an intra-pleural electrical impedance sensor embedded in the therapeutic chest tube (FIG. 1, 2) or a convex portion of chest tube to orient the electrodes toward the lung (FIG. 3) could confirm full expansion of the lung, detect the development of lung collapse (pneumothorax), and identify successful resolution of pneumothorax with restoration of complete lung expansion in real time. These results would apply clinically to the scenario in which a patient with an air leak from the lung underwent a trial of transition from suction to non-suction therapy, experienced pneumothorax development, and was returned to suction therapy with resolution of the pneumothorax. This was confirmed by radiologic examination of the pig thorax in the presence of 4 liters per minute air leak and alternation of the therapeutic chest tube between suction therapy and non-suction therapy (FIG. 4). The functionality of such a device was based on the fact that when the therapeutic chest tube was set to suction therapy and the lung was fully expanded as verified by chest radiograph (FIG. 4 (7)), the electrodes embedded in the therapeutic chest tube were fully contacting the surface of the lung and therefore the electrical impedance value detected by the electrodes in the therapeutic chest tube was a finite value and had a very distinct sinusoidal pattern associated with the normal lung ventilation cycle (FIG. 4 (8)). When the therapeutic chest tube was transitioned to non-suction therapy at this level of air leak pneumothorax developed rapidly as verified by chest radiograph (FIG. 4 (9, arrow); under these conditions the impedance value measured by the intra-pleural electrodes became infinite as visualized by a flat-line or rail at the highest resistance value measurable by the impedance measuring device being observed in the resistance graph (FIG. 4 (10)). This flat-line was due to separation of the electrodes from the lung surface by the air insufflation into the pleural space and produced a very distinct signal readily differentiated from normal conditions (FIG. 4 (10)). When suction therapy through the therapeutic chest tube was restored, pneumothorax evacuation was achieved rapidly as confirmed by chest radiography (FIG. 4 (11)); this was associated with the rapid resolution of infinite impedance and restoration of the sinusoidal electrical impedance pattern associated with the normal lung ventilation cycle (FIG. 4 (12)).

A microprocessor can be used to electronically interpret the impedance signal and automatically alter the suction status of the chest tube. This would represent the clinical scenario of a patient with a chest tube who develops pneumothorax when clinicians are not present. In this case the system described herein would alter the suction status of the chest tube automatically based on the electronic recognition of an abnormal impedance pattern (e.g., a signal pattern similar to that shown FIG. 4 (10) and without the need for direct clinician oversight.

In certain aspects, the system can include, but need not be limited to the following components: (i) a microcontroller unit (MCU), (ii) a suction control circuit, and (iii) an impedance measurement circuit (see FIG. 2). The MCU could be any component or system that executes programmed instructions. The MCU can be coupled to the suction control circuit and the impedance measurement circuit. The MCU can include a computer processing unit (CPU) and storage devices, such as register or memory. The MCU can receive or fetch, or transmit data to or from the suction control circuit and the impedance measurement circuit, as well as process data received to generate one or more results that may result in communication of instructions to other components of the system. The CPU can be configured to execute an operating system (OS) and the applications of the system. According to certain embodiments the system can employ a graphical user interface for interaction with the microcontroller. According to certain implementations, the graphical user interface may include a touch screen, in addition to a rotating or sliding control button, or some other technology performing equivalent adjustment functions that complies with the required purposes. The graphical user interface may be provided with a patient monitoring and surveillance screen, which displays details of the elements according to various aspects to the present disclosure.

The suction control circuit could be any circuit or control mechanism that enables the MCU to control the suction level delivered to the patient. In certain aspects a negative pressure "vacuum" is needed to affect adequate flow and removal of undesirable air or fluids. A suction catheter can be placed in the appropriate position with one or several holes at the end thereby allowing flow of fluid or gas to the outside of the body. Not having accurate control of the vacuum source can pull tissue into the suction catheter leading to injury and or damage to the tissue. Bleeding, perforation, and death of tissue may ensue along with serious clinical harm. Accordingly, the MCU will be configured to control the vacuum source and provide the needed modulation of that vacuum source.

The impedance measurement circuit could be any method for measuring impedance. This includes both impedance measurement systems based on 2-electrode measurements, 3-electrode measurements, 4-electrode measurements or a system involving a greater number of electrodes.

One example of such system is one having a 4-wire impedance measurement (FIG. 5) such as that used to demonstrate feasibility. A known alternating current (AC) stimulation current is driven on the outer electrodes of the chest tube (I+, and I−). The resulting AC voltage is measured on the inner electrodes (V+, V−). The impedance (Z) is then calculated by the following equation: Z=V/I (see FIG. 5). For the purpose of this system the digital suction control circuit was implemented using a power metal-oxide semiconductor field-effect transistor (MOSFET). The power MOSFET can be modulated by the MCU at a duty cycle that adjusts the power delivered to the suction motor and therefore controls the amount of suction delivered to the patient. A 50% duty cycle results in 50% power delivery to the suction motor. A 100% duty cycle results in 100% power being delivery to the suction motor. The duty cycle and suction level delivered to the patient are directly related. In short, a higher duty cycle results in an increased suction level.

The amount of power delivered to the suction device is modulated by the MCU based on the impedance value detected by the impedance measurement circuit. When the lung is fully expanded, the chest tube lying next to the lung in the pleural space is completely in contact with the lung, meaning the electrodes in the chest are fully in contact with the surface of the lung. In this situation, the electrical impedance value detected by the electrodes is a finite value and has a very distinct sinusoidal pattern associated with the normal lung ventilation cycle. In this situation, the MCU will decrease power to the suction motor since suction is not needed in this situation because no pneumothorax is present and the normal ventilation movement of the lung will maintain lung expansion. When pneumothorax is present, the electrodes lose contact with the lung surface and the electrical impedance value becomes infinite (this is because current ceases to flow between the electrodes due to loss of contact with the lung surface or with the inner lining of the rib cage). In this situation, the MCU again modulates power to the suction motor based on the impedance value detected by the impedance measurement circuit; however, due to the MCU recognizing an infinite impedance value the MCU will deliver full power to the suction motor for the purpose of evacuating the pneumothorax. The MCU will maintain suction until it recognizes restoration of the normal ventilation impedance signal; at that point, depending on the programming, it will either maintain full power to the suction motor or attempt to decrease power to the suction motor as a means of minimizing the suction delivered to the pleural space to reduce lung trauma.

Figure 6:
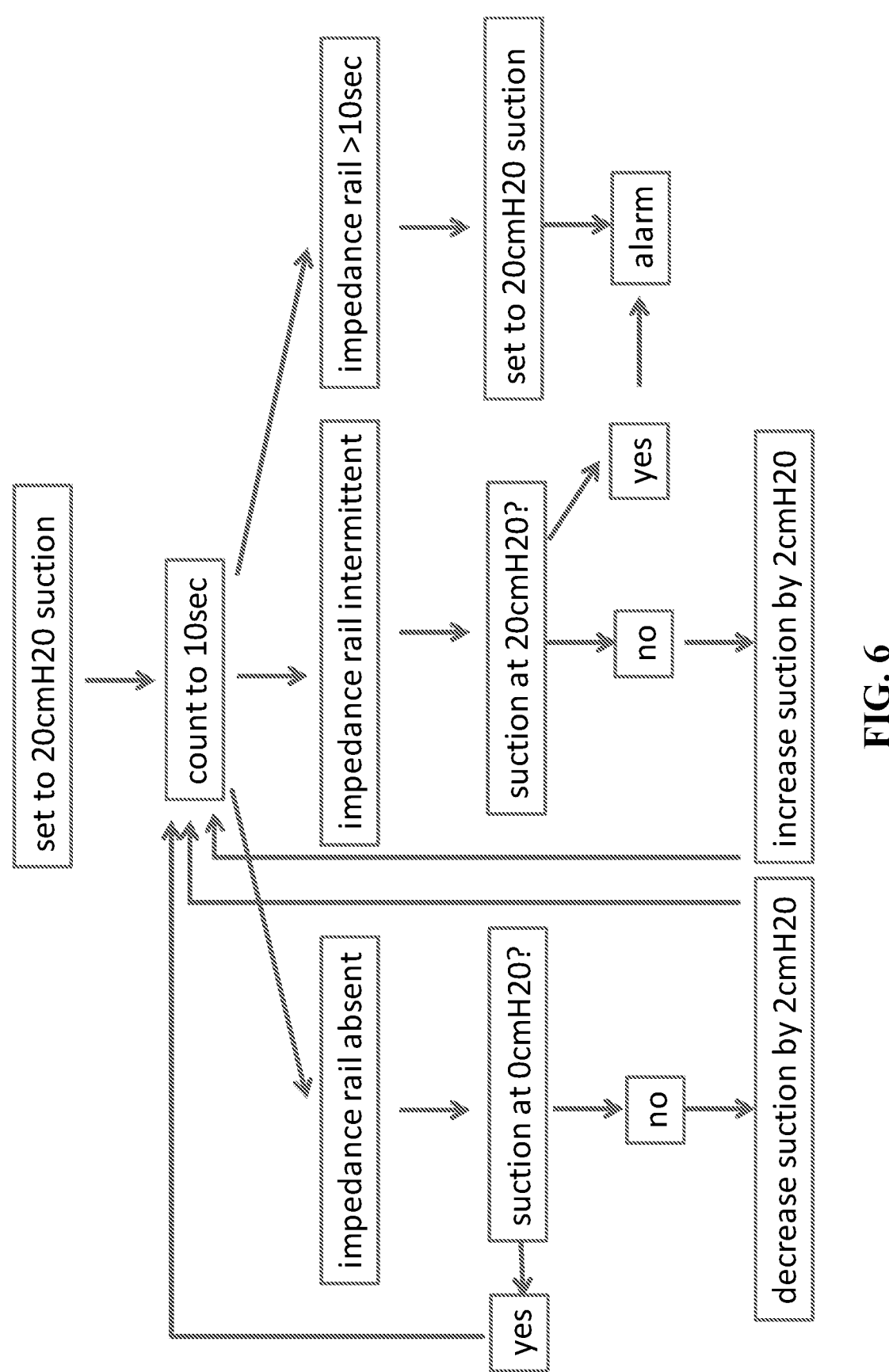
FIG. 6 is a flow chart diagraming one example of a monitoring scheme for patients having a chest tube.
Figure 7:
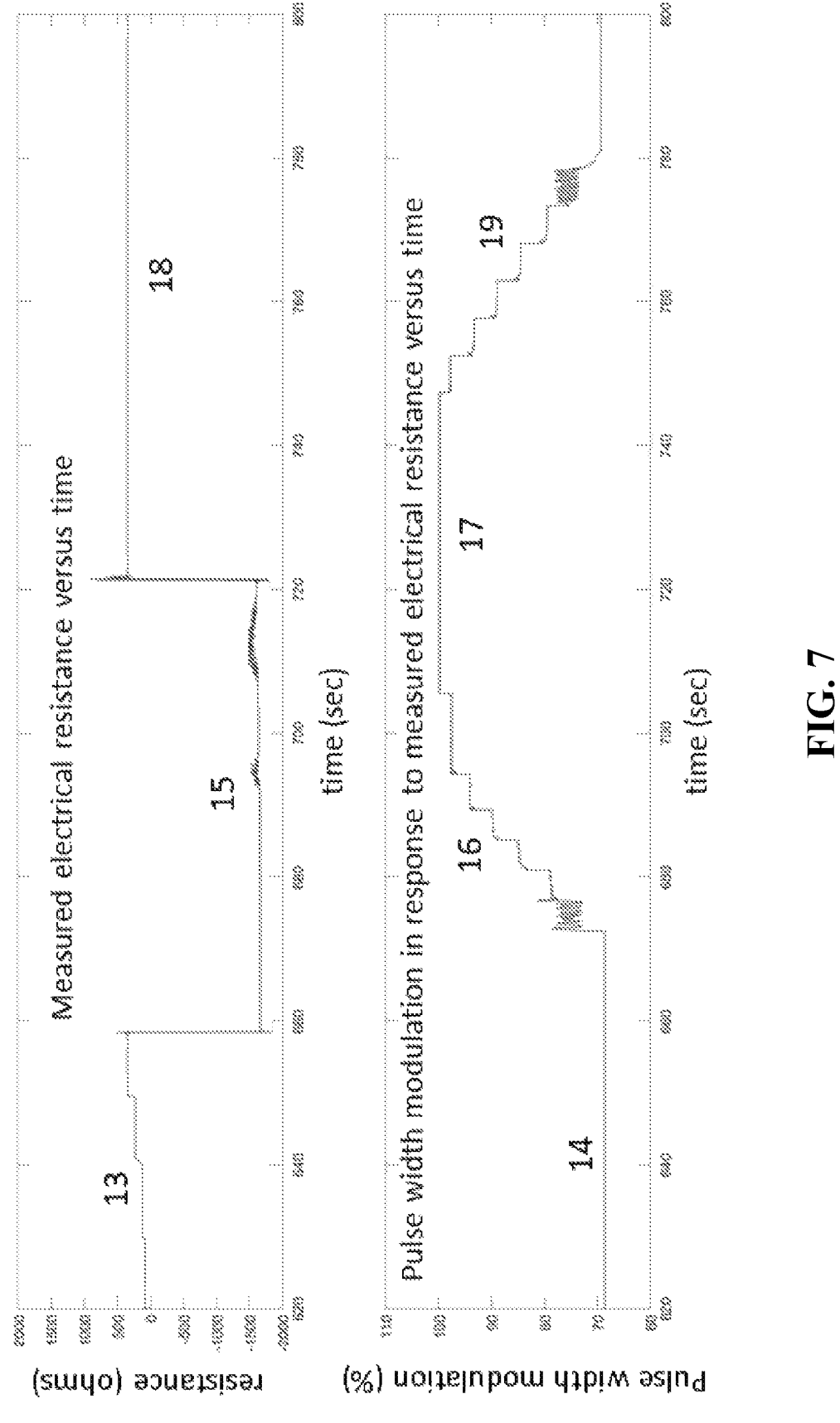
FIG. 7 is a graph demonstrating the action of the microprocessor to modulate current delivered to a suction pump in response to impedance changes detected by the impedance sensor of FIG. 1-3 in an ex vivo benchtop model.

An example flow chart of the functionality of the MCU/chest tube suction device is diagrammed in FIG. 6. A graph showing experimental results of this MCU in a bench top model of pneumothorax is provided in FIG. 7. In FIG. 7, the initial resistance value is a finite value between 0-500 ohms (13); under these circumstances the MCU sets a low (PWM) percentage current to the suction pump because low suction is sufficient (14). In FIG. 7 (15), the resistance becomes infinite, representing the loss of contact of the lung with the sensor; this is indicated in this resistance monitoring device by a flat-line or rail at the negative of the maximum resistance detectable by the monitoring device (approximately −1600 ohms) though in other resistance measuring devices it would be the positive value of the maximum resistance detectable by that device. The response of the MCU to this flat-line resistance pattern is to begin increasing the PMW percentage to the suction pump to increase the duty cycle of the pump to increase the level of suction delivered (16). This continues to one hundred percent PMW to achieve maximum suction from the pump while the resistance value remains infinite (17). In FIG. 7 (18), the detected resistance returns to a finite value between 0-500 ohms representing a restoration of full lung expansion. In response to these conditions, the MCU begins to decrease the PWM to the suction pump to decrease the amount of suction delivered (19), representing the attempt by the MCU to identify the minimum amount of suction required to maintain a finite resistance value within a determined range, in this case between 0-500 ohms.

Figure 5:
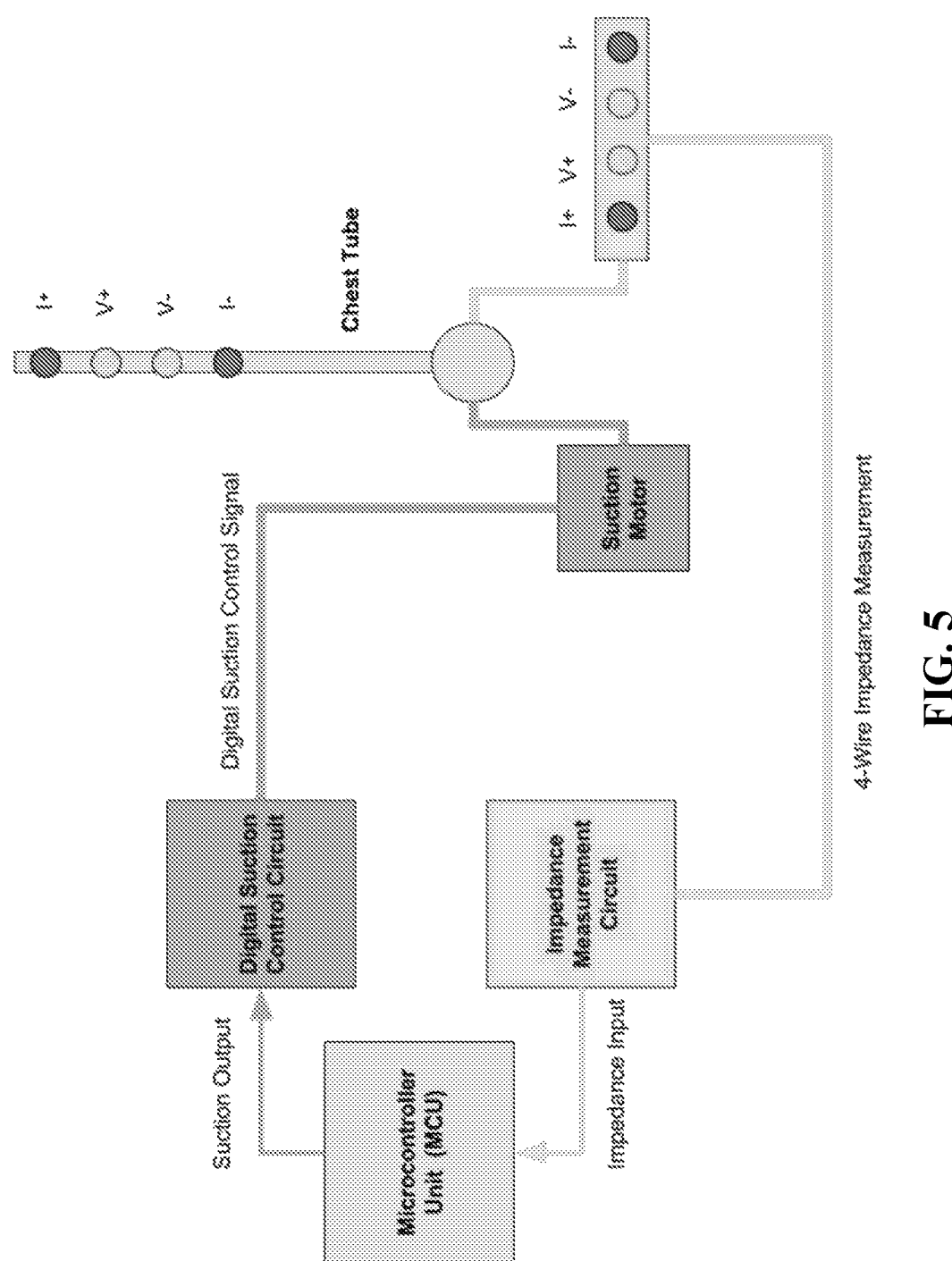
FIG. 5 is a diagram of a system of a physiologic feedback loop for monitoring and intervention of lung collapse.
Figure 8:
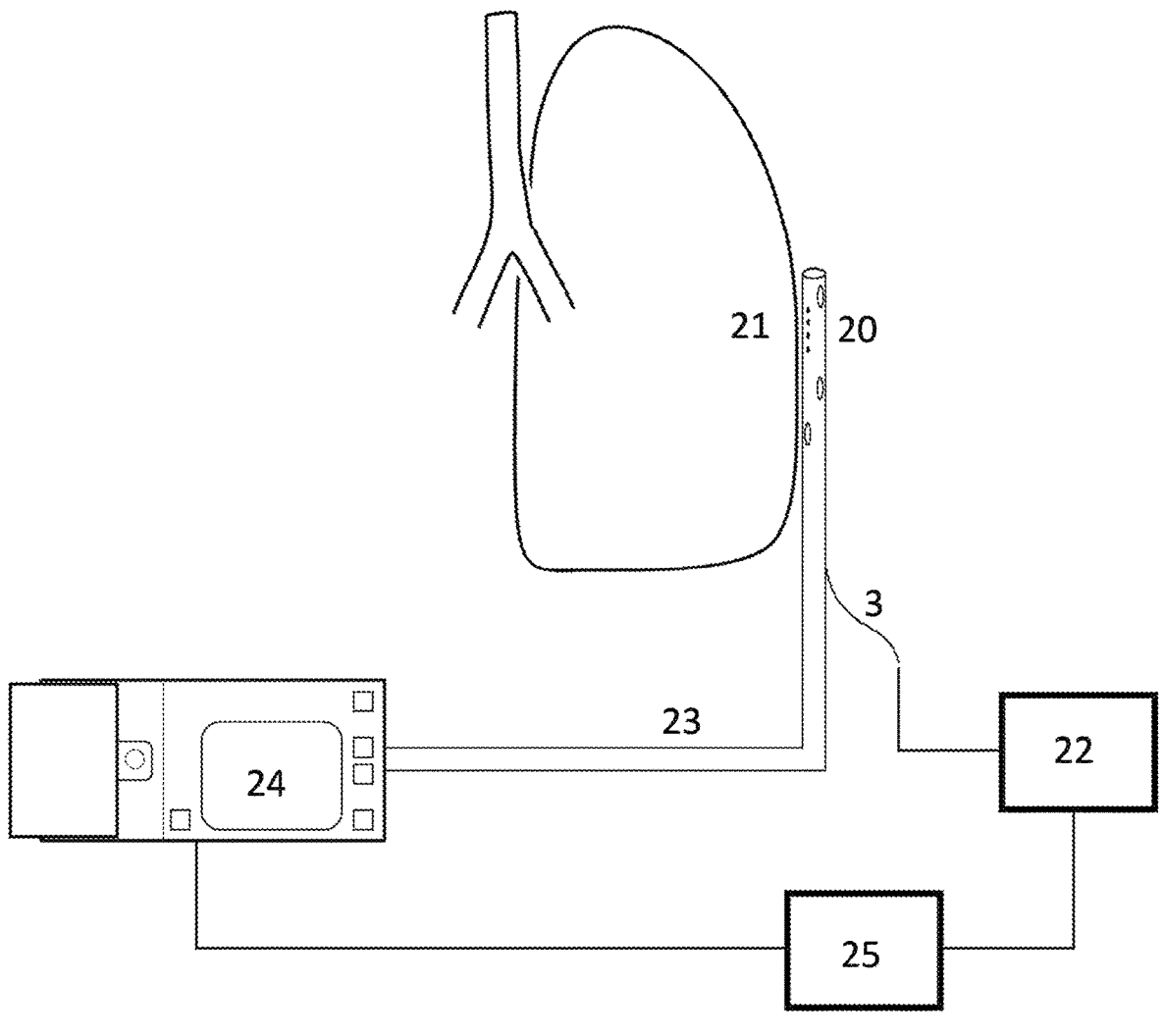
FIG. 8 is a schematic of the chest tube with impedance sensor/microprocessor/digital suction device physiologic feedback loop to modulate suction in response to impedance changes directed at pneumothorax detection by the impedance sensor of FIG. 1-3 in an in vivo porcine model.

The 4-wire impedance measurement system depicted in FIG. 5 was tested in a porcine model of air leak similar to that described above in association with FIG. 4 to demonstrate the feasibility of such a system. A schematic of this animal model is shown in FIG. 8. FIG. 8 (20) indicates a chest tube with embedded electrodes as described in FIG. 1 and FIG. 2 with electrodes contacting the surface of the lung (FIG. 8 (21)) and with connecting wires (3) connecting to an impedance measurement circuit (22). The chest tube (20) was further connected by connecting tubing (23) to a digital suction device (24) which applied either active suction or non-suction one-way valve functionality to the chest tube (20). Not shown in this figure is a second chest tube which was placed to deliver air leak at determined rates to mimic an active air leak from the lung. The impedance measuring circuit was further connected to a microcontroller unit (MCU) (25) which in turn was connected to the digital suction device (24), This configuration allowed the impedance signal detected by the chest-tube embedded electrodes (20) to be communicated to the MCU (25) in order for the MCU to electronically determine suction versus non-suction therapy and/or the level of suction delivered by the digital suction device (24).

Graphs showing experimental results of this MCU/chest tube suction device in an animal model of pneumothorax are demonstrated in FIG. 9-12. For these experiments, the animal model described above for FIG. 8 was used consisting of two chest tubes located in the pleural space of a pig. One chest tube was meant to represent a conventional, therapeutic chest tube as used in human patients, which is connected to a one way valve and/or suction which allows any air present in the pleural space to be removed, maintaining full lung expansion; this chest tube also contained the embedded electrodes as described in FIG. 1 and FIG. 2 with electrodes contacting the surface of the lung (FIG. 8 (21). The second tube was used to introduce air into the pleural space at defined air-flows to mimic a pathologic air leak from the lung.

Figure 9:
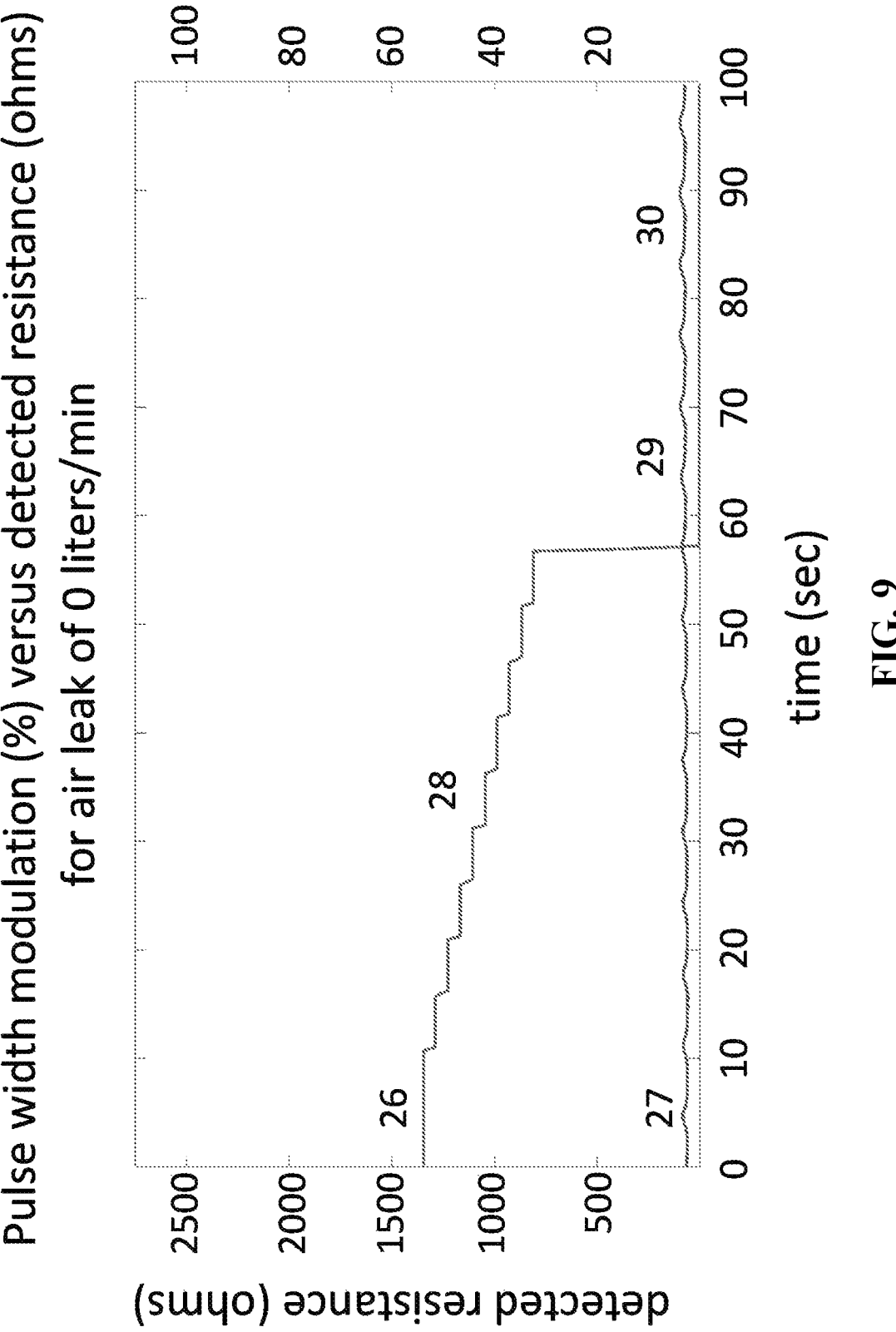
FIG. 9 is a graph demonstrating the action of the microprocessor to modulate current delivered to a suction pump in response to impedance changes detected by the impedance sensor of FIG. 1-3 in an in vivo porcine model.

FIG. 9 shows experimental results of an experiment in which no air leak was present. In FIG. 9 the PMW of the MCU was initially set at approximately 55% (26) and a finite resistance value, normal respiratory resistance waveform (27) was detected by the pleural sensor. The programmed algorithm of the MCU then prompted a steady interval decrease in the PMW (28) until the PMW went to a value of 0% (29). At time point (30), a finite resistance value, normal respiratory resistance waveform was detected by the pleural sensor resulting in the MCU continuing a PMW of 0% according to the algorithm. This experiment demonstrated that, in the case of no pleural air leak, non-suction therapy can be successful at maintaining full lung expansion, that the intrapleural impedance sensor can accurately confirm full lung expansion, and that the measured impedance values can be transmitted to an MCU which in turn can command the suction device to maintain a PMW of 0% in the setting of full lung expansion in the absence of direct human intervention.

Figure 10:
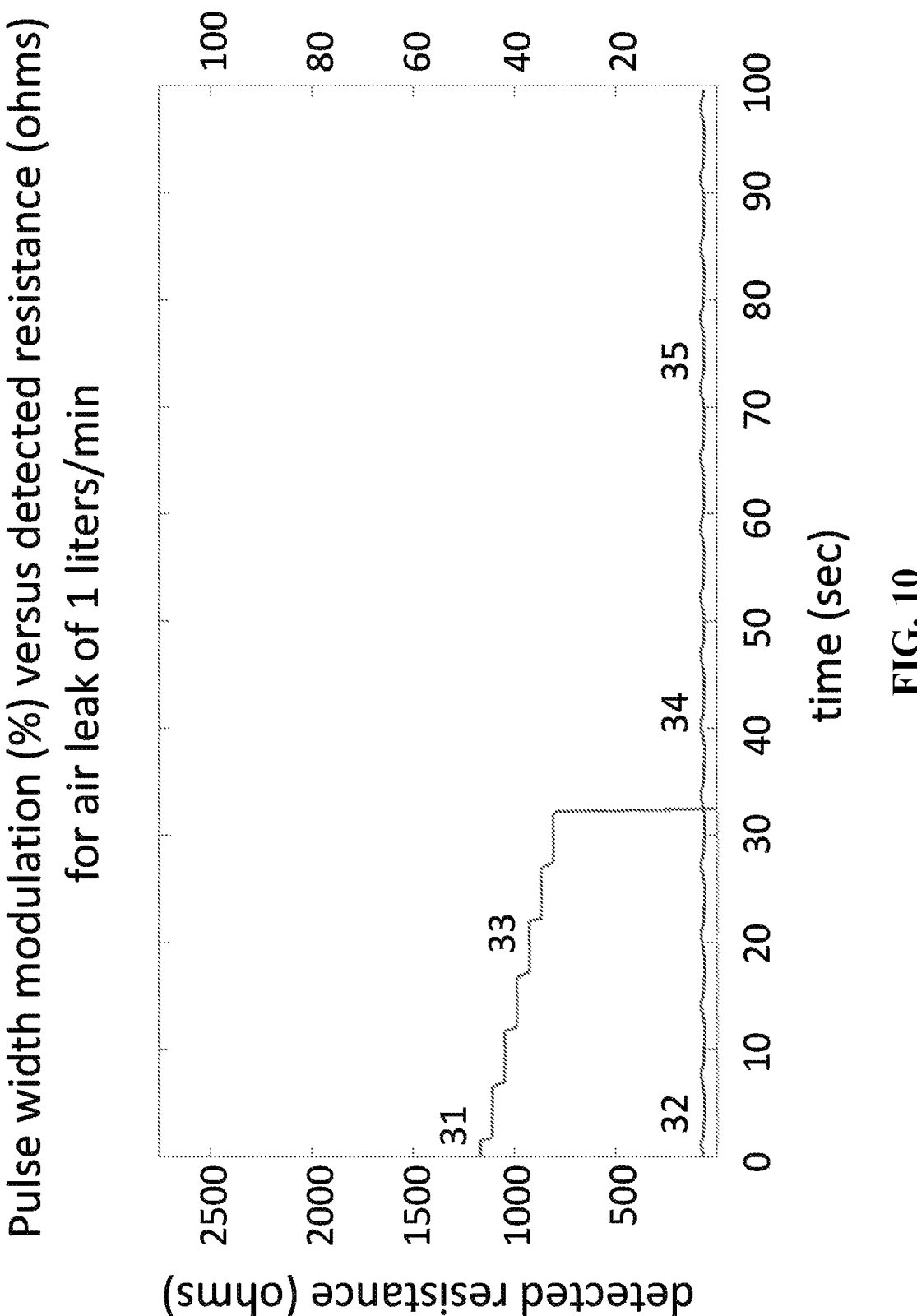
FIG. 10 is a graph demonstrating the action of the microprocessor to modulate current delivered to a suction pump in response to impedance changes detected by the impedance sensor of FIG. 1-3 in an in vivo porcine model.

FIG. 10 shows experimental results of an experiment in which 1 liter/min air leak was present. In FIG. 10 the PMW of the MCU was initially set at approximately 50% (31) and a finite resistance value, normal respiratory resistance waveform (32) was detected by the pleural sensor. The programmed algorithm of the MCU then prompted a steady interval decrease in the PMW (33) until the PMW went to a value of 0% (34). At time point (35), a finite resistance value, normal respiratory resistance waveform was detected by the pleural sensor resulting in the MCU continuing a PMW of 0% according to the algorithm. This study demonstrates that, in the case of small air leaks, non-suction therapy can be successful at maintaining full lung expansion, that the intrapleural impedance sensor can accurately confirm full lung expansion, and that the measured impedance values can be transmitted to an MCU which in turn can command the suction device to maintain a PMW of 0% in the setting of full lung expansion in the absence of direct human intervention.

Figure 11:
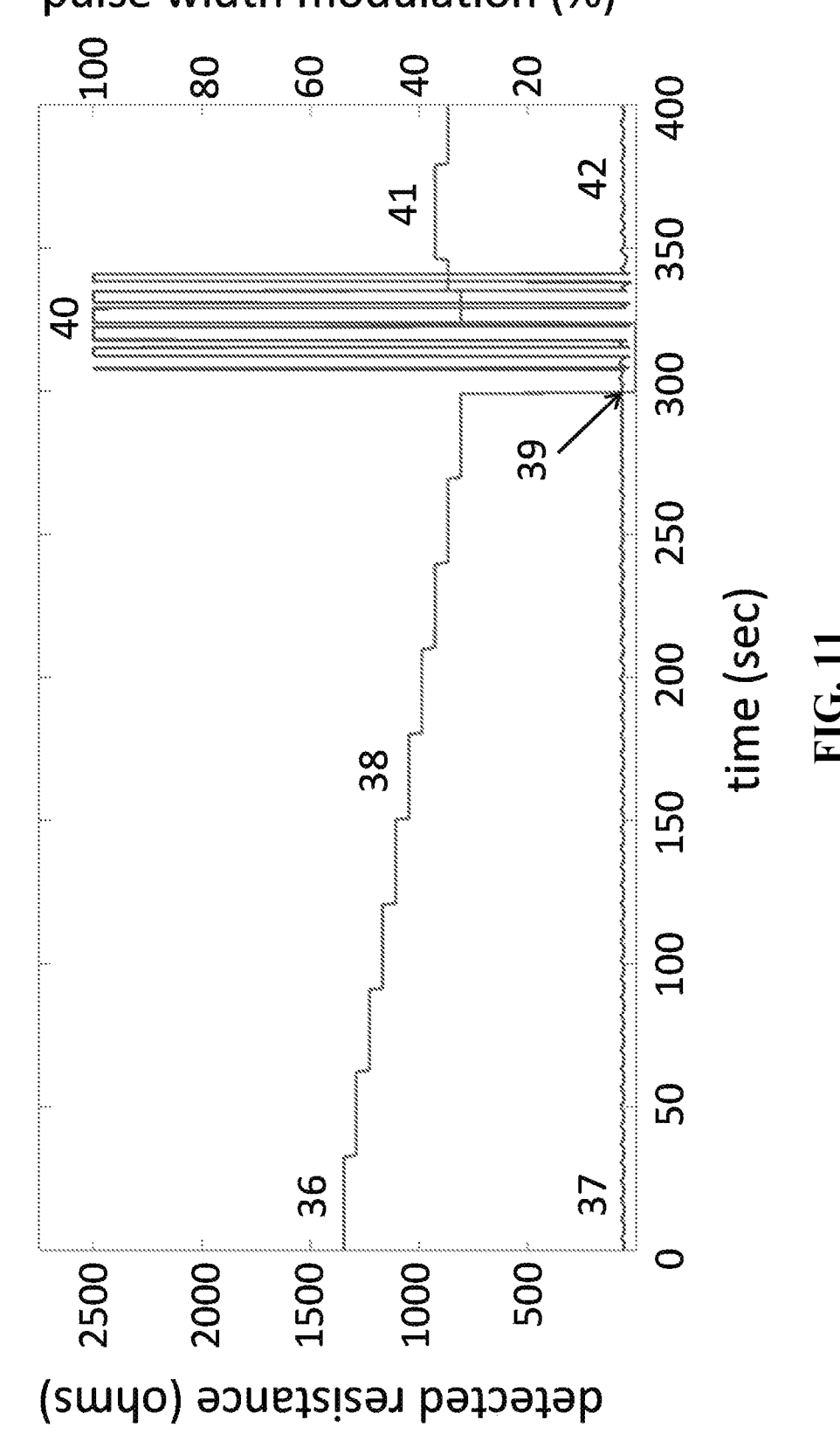
FIG. 11 is a graph demonstrating the action of the microprocessor to modulate current delivered to a suction pump in response to impedance changes detected by the impedance sensor of FIG. 1-3 in an in vivo porcine model.

FIG. 11 shows experimental results of an experiment in which 4 liter/min air leak was present. In FIG. 11 the PMW of the MCU was initially set at approximately 55% (36) and a finite resistance value, normal respiratory resistance waveform (37) was detected by the pleural sensor. The programmed algorithm of the MCU then prompted a steady interval decrease in the PMW (38) until the PMW went to a value of 0% (39, arrow). At time point (40), infinite resistance and loss of the normal respiratory resistance waveform were detected by the pleural sensor resulting in the MCU returning to a PMW required to restore a finite resistance, normal respiratory resistance waveform (approximately 40%) (41) according to the programmed algorithm; this resulted in the restoration of the finite resistance, normal respiratory resistance waveform at time point (42). This experiment demonstrated that, in the case of moderate air leaks, non-suction therapy can be attempted to maintain full lung expansion but if the intrapleural impedance sensor identifies the failure of non-suction therapy, i.e. the development of pneumothorax, the infinite impedance values measured by the sensor can be transmitted to an MCU which in turn can command the suction device to restore suction therapy to re-establish a normal, finite respiratory impedance waveform in the absence of direct human intervention.

Figure 12:
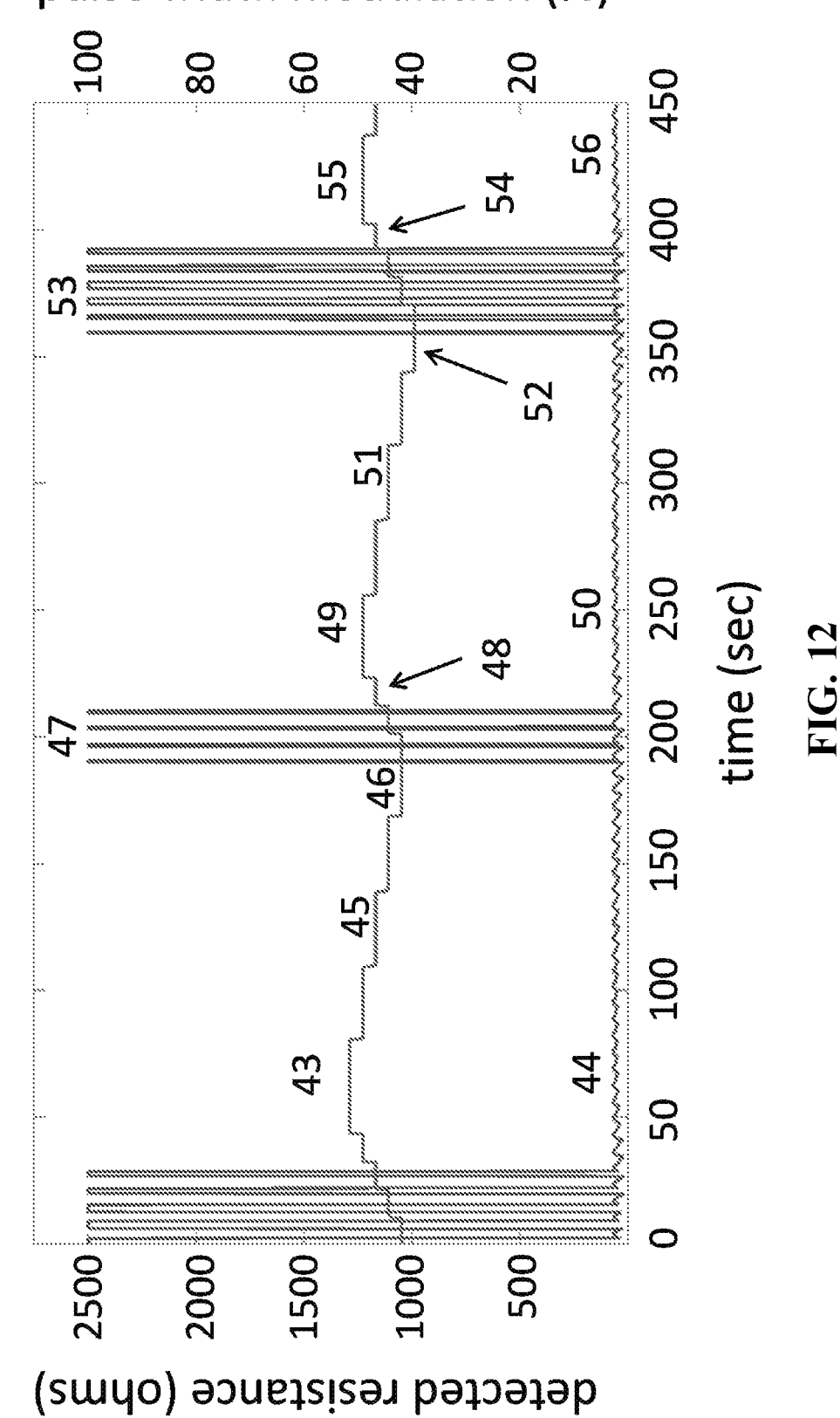
FIG. 12 is a graph demonstrating the action of the microprocessor to modulate current delivered to a suction pump in response to impedance changes detected by the impedance sensor of FIG. 1-3 in an in vivo porcine model.

FIG. 12 shows experimental results of an experiment in which 6 liter/min air leak was present. In FIG. 12 the PMW of the MCU was initially set at approximately 55% (43) and a finite resistance value, normal respiratory resistance waveform (44) was detected by the pleural sensor. The programmed algorithm of the MCU then prompted a steady interval decrease in the PMW (45) until the PMW went to a value of 40% (46). At this level of PMW, however, the suction was no longer capable of evacuating the air introduced by the air leak and pneumothorax developed as indicated by infinite resistance and loss of the normal respiratory resistance waveform being detected by the pleural sensor (47). This resulted in the MCU increasing the PMW (48) according to the programmed algorithm back to approximately 50% (49) which was the amount of power required to restore a finite resistance, normal respiratory resistance waveform (50). According to the programmed algorithm, the restoration of a finite resistance, normal respiratory resistance waveform (50) resulted in the MCU attempting again to reduce PMW (51) as a means of reducing the amount of suction therapy delivered to the experimental animal to a level of about 40% PMW (52). However, as before, at this level of PMW, the suction was no longer capable of evacuating the air introduced by the air leak and pneumothorax again developed as indicated by infinite resistance and loss of the normal respiratory resistance waveform being detected by the pleural sensor (53). This resulted in the MCU increasing the PMW (54) according to the programmed algorithm back to approximately 50% (55) which was the amount of power required to restore a finite resistance, normal respiratory resistance waveform (56). This experiment demonstrated that, in the case of large air leaks, suction therapy can still be minimized to maintain full lung expansion but if the intrapleural impedance sensor identifies the failure at a certain point of reducing suction, i.e. the development of pneumothorax, the infinite impedance values measured by the sensor can be transmitted to an MCU which in turn can command the suction device to restore full suction therapy and that the MCU, according to the programmed algorithm will continue to try to identify the lowest amount of suction required to maintain a normal, finite respiratory impedance waveform in the absence of direct human intervention.

Figure 13:
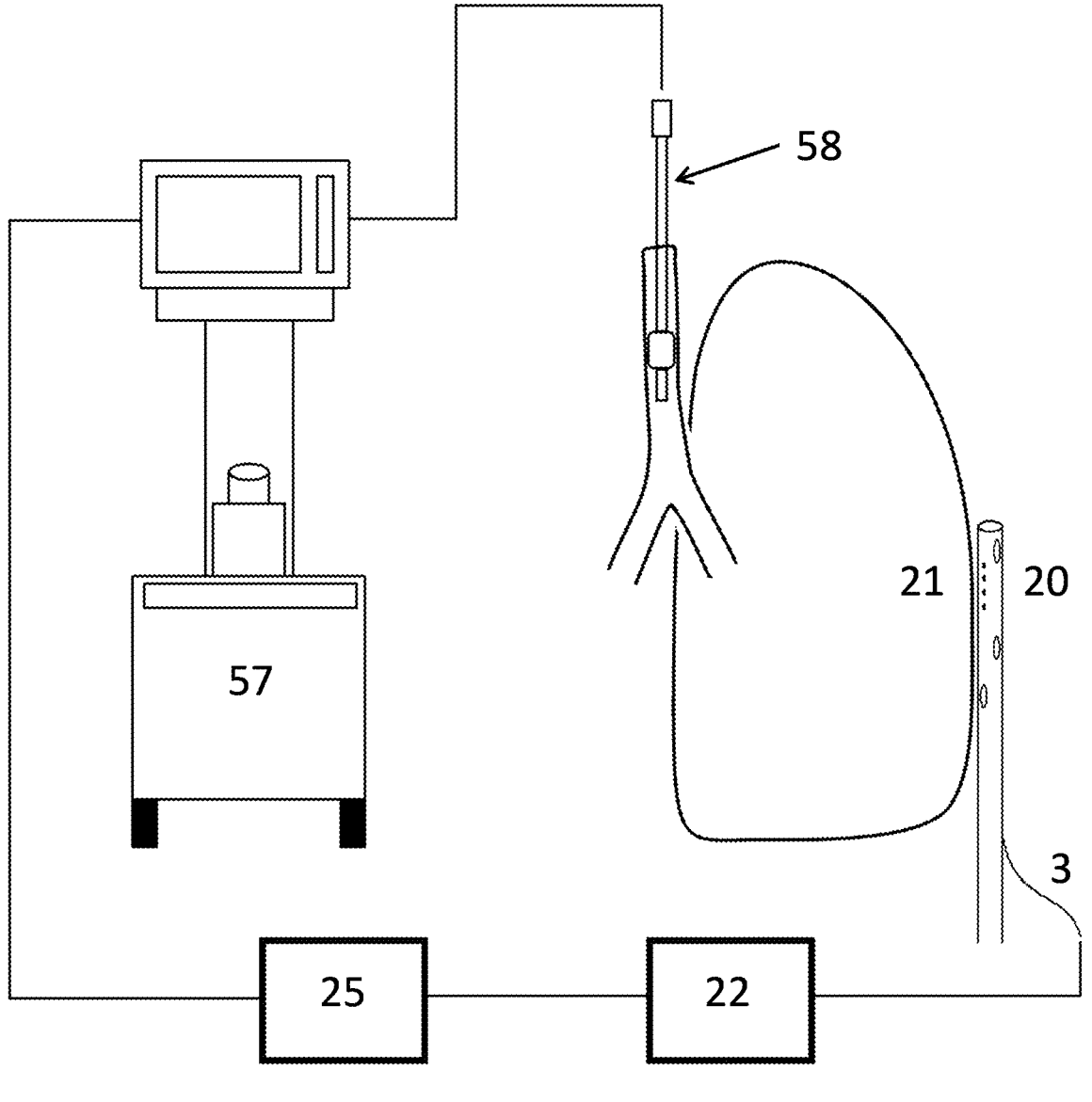
FIG. 13 is a schematic of the chest tube with impedance sensor/microprocessor/mechanical ventilator physiologic feedback loop to modulate delivered tidal volume in response to impedance changes directed at regional lung ventilation detection by the impedance sensor of FIG. 1-3 in an in vivo porcine model.

The 4-wire impedance measurement system depicted in FIG. 5 was also tested in a porcine model of regional lung ventilation to demonstrate the feasibility of such a system. A schematic of this animal model is shown in FIG. 13. FIG. 13 (20) indicates a chest tube with embedded electrodes as described in FIG. 1&2 with electrodes contacting the surface of the lung (FIG. 13 (21)) and with connecting wires (3) connecting to an impedance measurement circuit (22). The chest tube (20) was further connected to a suction device (not shown) to assure the maintenance of full lung expansion. The impedance measuring circuit was further connected to a microcontroller unit (MCU) (25) which in turn was connected to a mechanical ventilator (57) which was in turn delivering defined respiratory tidal volumes to the lung (21) via an endotracheal tube (58), The mechanical ventilator (57) had a built in capacity to identify the peak inspiratory pressure ($P_{IP}$) associated with each defined delivered tidal volume. Using the impedance values obtained by the impedance measurement circuit (22), the impedance amplitude defined by ($R_P$–$R_T$) and in turn the aeration index defined by ($R_P$–$R_T$)/($P_{IP}$) could be calculated for each defined delivered tidal volume. This configuration allowed the impedance signal detected by the chest-tube embedded electrodes (20) and the peak airway pressure detected by the mechanical ventilator (57) to be communicated to the MCU (25) in order for the MCU to electronically determine optimal tidal volume delivery as a function of the maximization of the aeration index.

Figure 14:
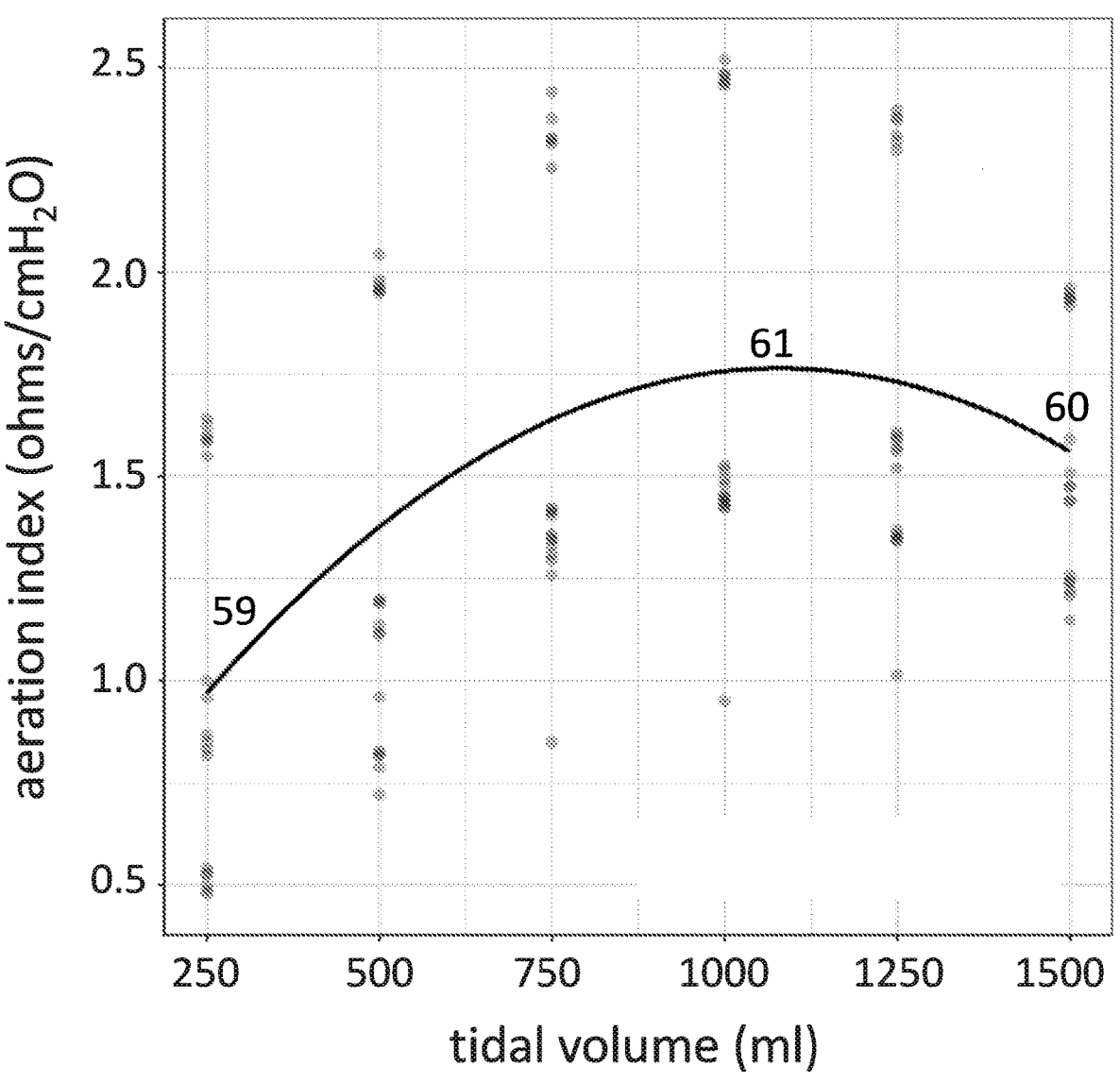
FIG. 14 is a graph demonstrating the action of the modulation of mechanical ventilator-delivered tidal volume in response to changes in aeration index $(R_P–R_T)/P_{IP}$ detected by the impedance sensor of FIG. 1-3 in an in vivo porcine model.

FIG. 14 shows experimental results of an experiment in an animal model of optimization of regional lung ventilation using the configuration illustrated in FIG. 13. For this experiment, the animal model consisted of the chest tube with embedded electrodes illustrated in FIG. 1-2 located in the pleural space of a pig being ventilated by a mechanical ventilator. The chest tube was meant to represent a conventional, therapeutic chest tube as used in human patients, i.e., which is connected to a one way valve and/or suction which allows any air present in the pleural space to be removed, maintaining full lung expansion. The electrodes in the chest tube were directed to face the surface of the lung and to be insulated away from the rib cage. The tidal volume delivered by the mechanical ventilator was modulated manually throughout a range from 250-1500 milliliters. At each tidal volume, the aeration index (AI) given by ($R_P$–$R_T$)/$P_{IP}$ was calculated and graphed. This graph demonstrated that the value of AI was relatively low at low tidal volumes (FIG. 14 (59)) and high tidal volumes (60) but attained a maximum value at an intermediate tidal volume (61) which indicated the tidal volume of maximum regional ventilatory efficiency. While in this experiment tidal volume was modulated manually, in an embodiment, the MCU could be used to calculate AI based on measured impedance values and make adjustments to delivered tidal volume automatically to maximize regional lung ventilation continuously in real time.

Figure 15:
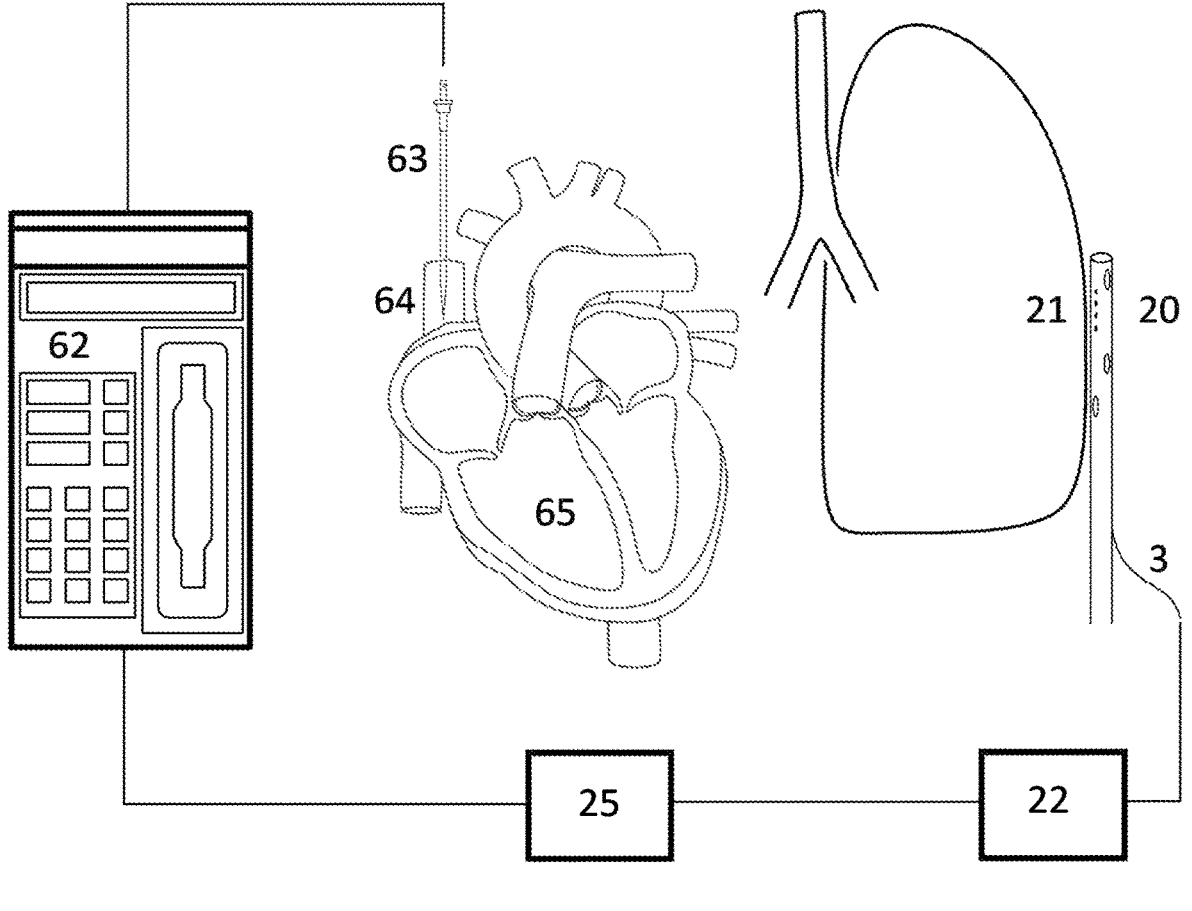
FIG. 15 is a schematic of the chest tube with impedance sensor/microprocessor/intravenous fluid pump feedback loop to modulate intravenous diuretic medication, ionotrope, and/or intravenous fluid delivery in response to impedance changes directed at pulmonary edema detection by the impedance sensor of FIG. 1-3.

A schematic of an in vivo model for a physiologic feedback loop for the detection and treatment of pulmonary edema by the 4-wire impedance measurement system (see e.g., FIG. 5) is shown in FIG. 15. FIG. 15 (20) indicates a chest tube with embedded electrodes as described in FIG. 1 and FIG. 2 with electrodes contacting the surface of the lung (21) and with connecting wires (3) connecting to an impedance measurement circuit (22). The chest tube (20) is further connected to a suction device (not shown) to assure the maintenance of full lung expansion. The impedance measuring circuit (22) is further connected to a microcontroller unit (MCU) (25) which in turn is connected to an intravenous pump (62) for delivery of diuretic medications, inotropic medications, and/or intravenous fluids via an intravenous line, in the case of FIG. 15, a central intravenous line (63) delivering medications or fluids into the superior vena cava (64) of the heart (65). This configuration would allow for the impedance signal detected by the chest-tube embedded electrodes (20) to be communicated to the MCU (25) in order for the MCU to electronically determine the need to increase or decrease delivery of diuretic medications, inotropic medications, and/or intravenous fluids based on the degree of pulmonary edema and then signal the intravenous pump to carry out the action without the need for human intervention. The impedance signal associated with greater or lesser degrees of pulmonary edema would be a relatively or absolutely lower or higher electrical impedance respectively as detected from the surface of the lung.

Figure 16:
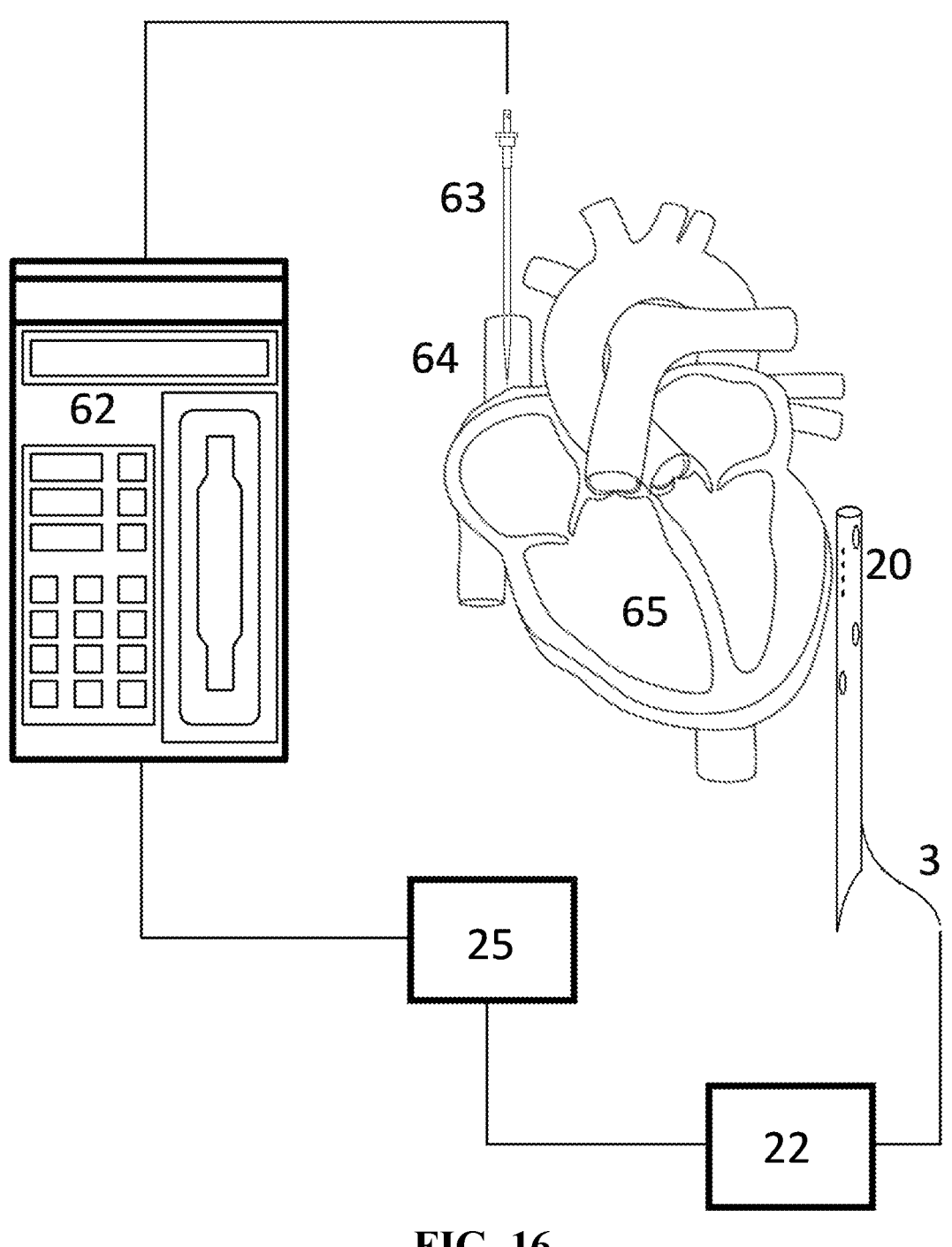
FIG. 16 is a schematic of the chest tube with impedance sensor/microprocessor/intravenous fluid pump feedback loop to modulate intravenous diuretic medication, ionotrope, and/or intravenous fluid delivery in response to impedance changes directed at cardiac contractility detection by the impedance sensor of FIG. 1-3.

A schematic of an in vivo model for a physiologic feedback loop for the detection and optimization of cardiac contractility by the 4-wire impedance measurement system (e.g., FIG. 5) is shown in FIG. 16. FIG. 16 (20) indicates a chest tube with embedded electrodes as described in FIG. 1 and FIG. 2 with electrodes contacting the surface of the heart (65) and with connecting wires (3) connecting to an impedance measurement circuit (22). The chest tube (20) is further connected to a suction device (not shown). The impedance measuring circuit (22) is further connected to a microcontroller unit (MCU) (25) which in turn is connected to an intravenous pump (62) for delivery of diuretic medications, inotropic medications, or intravenous fluids via an intravenous line, in the case of FIG. 16, a central intravenous line (63) delivering medications or fluids into the superior vena cava (64) of the heart (65). This configuration would allow for the impedance signal detected by the chest-tube embedded electrodes (20) to be communicated to the MCU (25) in order for the MCU to electronically determine the need to increase or decrease delivery of diuretic medications, inotropic medications, and/or intravenous fluids based on the improvement or worsening of cardiac contractility and then signal the intravenous pump to carry out the action without the need for human intervention. The impedance signal associated with poor cardiac contractility could be a relatively lower impedance in the setting of hypovolemia or relatively higher impedance in the setting of congestive heart failure as detected from the surface of the heart or could be associated with a loss of the normal cardiac cycle pattern of impedance from the heart in the case of pericardial tamponade.

The studies illustrated in FIG. 9-12 demonstrate the ability of the MCU/chest tube device to minimize delivered suction therapy while full lung expansion is present but also to respond to the development of pneumothorax by increasing delivered suction therapy.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra-density optical discs, any other optical or magnetic media, and floppy disks. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code).

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

The invention claimed is:

1. A method for detecting lung collapse in a subject having a chest tube or other device implanted into the pleural space wherein a monitoring system comprising an impedance measuring circuit, a suction control circuit, and microcontroller performs steps comprising:

a. determining initial impedance measured by a sensor in the chest cavity to determine presence or absence of impedance rail signal in the impedance measurement;

b. continuing monitoring if no impedance rail is detected or applying suction for a predetermined period of time if an impedance rail is detected for a pre-determined period of time without suction;

c. reducing suction after a pre-determined period of time;

d. determining impedance after suction is reduced and determine presence or absence of impedance rail signal in impedance measurement; and e. continue monitoring if no impedance rail is detected or applying suction if impedance rail signal is detected for a pre-determined period of time and repeat steps (c) and (d).

2. The method of claim 1, wherein the predetermined period of time for applying suction in step (b) is 10 seconds +/−0.5 seconds if an impedance rail is detected for longer than 10 seconds without suction.

3. The method of claim 1, wherein the suction in step (c) is reduced after 10 seconds.

4. The method of claim 1, wherein suction in step (e) is applied if an impedance rail signal is detected for greater than 10 seconds.

5. The method of claim 1, further comprising initiating suction at a pre-determined level of suction, preferably 0 to 40 cm $H_2O$.

6. The method of claim 5, wherein the suction is reduced by some pre-determined amount, preferably 0 to 2 cm $H_2O$, if no impedance rail signal is detected.

7. The method of claim 1, further comprising applying suction when intermittent rail signal is detected of some pre-determined amount, preferably 5 to 10 cm $H_2O$.

8. The method of claim 7, further comprising increasing the suction by some predetermined amount, preferably 2 cm $H_2O$, if intermittent impedance rail signal continues.

9. The method of claim 1, where monitoring is continuous.

10. A method for detecting regional lung ventilation in a subject (i) ventilated by a mechanical ventilator, (ii) having a chest tube or other device implanted into the pleural space with the ability to measure electrical impedance from the surface of the lung and (iii) having a pressure sensor measuring intra-airway pressure comprising monitoring the subject with a monitoring system comprising a sensor for measuring airway pressure, an impedance measuring circuit, a mechanical ventilator control circuit, and microcontroller, monitoring steps comprising:

a. determining initial intra-airway pressure, initial peak lung impedance, initial average lung impedance, and initial amplitude of the respiratory impedance waveform measured by the sensors in the chest cavity to determine the degree of regional lung ventilation and calculating a value for the aeration index (AI) as given by: $(R_P{-}R_T)/P_{IP}$ or $(Z_P{-}Z_T)/P_{IP}$;

b. reducing or increasing ventilator tidal volume according to a pre-determined algorithm after a pre-determined period of time;

c. determining intra-airway pressure, peak lung impedance, average lung impedance, and amplitude of the respiratory impedance waveform and from these calculating the value for aeration index (AI) after tidal volume is reduced or increased and determine whether regional lung ventilation 1s improved or diminished with respect to intra-airway pressure; and d. continue monitoring if regional lung ventilation is improved with respect to intra-airway pressure based on the value for AI or reducing or increasing tidal volume according to a pre-determined algorithm for a pre-determined period of time and repeat steps (b) and (c).

11. A method for detecting pulmonary edema in a subject having a chest tube or other device implanted into the pleural space using a monitoring system comprising an impedance measuring circuit, a control circuit controlling diuretic medication and/or inotrope administration and/or intravenous fluid administration, and microcontroller to perform the steps comprising:

a. determining initial lung impedance as measured by a sensor in the chest cavity to determine the degree of pulmonary edema;

b. administering diuretic medication and/or inotropes and/or intravenous fluids by a predetermined algorithm after a pre-determined period of time;

c. determining lung impedance after diuretic medication and/or inotrope and/or intravenous fluid delivery and determine whether pulmonary edema is increased or decreased; and d. continue monitoring if pulmonary edema is increased or decreased or administer diuretic medications and/or inotropes and/or intravenous fluids according to a pre-determined algorithm for a pre-determined period of time and repeat steps (b) and (c).

12. A method for detecting cardiac contractility in a subject having a chest tube or other device implanted into the pleural or pericardial space using a monitoring system comprising an impedance measuring circuit, a control circuit controlling diuretic medication and/or inotrope and/or vasopressor and/or intravenous fluid administration, and microcontroller by performing the steps comprising:

a. determining initial cardiac impedance as measured by a sensor in the chest cavity to determine the degree of cardiac contractility;

b. administering diuretic medication and/or inotropes and/or vasopressors and/or intravenous fluids by a pre-determined algorithm after a pre-determined period of time;

c. determining impedance after diuretic medication and/or inotrope and/or vasopressor and/or intravenous fluid delivery and determine whether cardiac contractility is increased or decreased; and d. continue monitoring if cardiac contractility is increased or decreased or administer diuretic medications and/or inotropes and/or vasopressors and/or intravenous fluids according to a pre-determined algorithm for a pre-determined period of time and repeat steps (b) and (c).

* * * * *